US012322513B2

United States Patent
Holcombe et al.

(10) Patent No.: US 12,322,513 B2
(45) Date of Patent: Jun. 3, 2025

(54) METHOD OR SYSTEM FOR DIAGNOSING PERIODONTAL DISEASE

(71) Applicant: MARS, INCORPORATED, McLean, VA (US)

(72) Inventors: Lucy Jane Holcombe, Leicestershire (GB); Paul Martin McGenity, West Yorkshire (GB); Phillip Martin McGenity, West Yorkshire (GB); Corryn Victoria Wallis, Leicestershire (GB)

(73) Assignee: MARS, INCORPORATED, McLean, VA (US)

( * ) Notice: Subject to any disclaimer, the term of this patent is extended or adjusted under 35 U.S.C. 154(b) by 655 days.

(21) Appl. No.: 17/293,791

(22) PCT Filed: Nov. 15, 2019

(86) PCT No.: PCT/US2019/061782
§ 371 (c)(1),
(2) Date: May 13, 2021

(87) PCT Pub. No.: WO2020/102710
PCT Pub. Date: May 22, 2020

(65) Prior Publication Data
US 2022/0005607 A1    Jan. 6, 2022

(30) Foreign Application Priority Data

Nov. 15, 2018   (GB) ................................. 1818627

(51) Int. Cl.
*G16H 50/30* (2018.01)
*G16H 20/60* (2018.01)
*G16H 50/20* (2018.01)
*A61B 10/00* (2006.01)

(52) U.S. Cl.
CPC ............ *G16H 50/30* (2018.01); *G16H 20/60* (2018.01); *G16H 50/20* (2018.01); *A61B 10/0051* (2013.01); *A61B 2503/40* (2013.01)

(58) Field of Classification Search
CPC ........ G16H 50/30; G16H 50/20; G16H 20/60; G16H 50/00; G16H 50/70; G16H 10/40;
(Continued)

(56) References Cited

U.S. PATENT DOCUMENTS 6,156,355 A  *  12/2000  Shields, Jr. ............. A23K 10/30
426/805
2008/0226766 A1*  9/2008  Fretwell .................... A61P 1/00
424/234.1

FOREIGN PATENT DOCUMENTS

AU    2012216582 B2 *  7/2013 ......... A46B 15/0002
WO    WO-2014097044 A1 *  6/2014 ........... A61K 36/575

OTHER PUBLICATIONS

Harvey, "Periodontal Disease in Dogs," Veterinary Clinics Of North America: Small Animal Practice, 28(5):1111-1128 (1998).
(Continued)

*Primary Examiner* — James J Yang
*Assistant Examiner* — Anthony D Afrifa-Kyei
(74) *Attorney, Agent, or Firm* — Baker Botts L.L.P.

(57) ABSTRACT

A method or system for determining the susceptibility of a dog to periodontal disease and to the development of treatment regimens based upon the levels of susceptibility determined. The method can include determining a characteristic of the dog selected from at least one of a breed of the dog, a shape of the dog's head, a size category of the dog, a weight or body condition of the dog, a predicted size category or weight of the dog as an adult, or an age of the dog. The method can also include comparing the characteristic with a dataset comprising an occurrence of the periodontal disease in other dogs having the at least one char-
(Continued)

acteristic. In addition, the method can include detecting an overall susceptibility level of the dog for the periodontal disease, and/or displaying a customized recommendation on a graphical user interface of the computer based on the overall susceptibility level of the dog.

11 Claims, 11 Drawing Sheets

(58) Field of Classification Search
CPC ............... G16H 20/30; A61B 10/0051; A61B 2503/40; A61B 5/0002; G06Q 50/00; G16B 50/00; G16B 50/20; G16B 50/30; G16B 50/40; Y02A 90/10
See application file for complete search history.

(56) References Cited

OTHER PUBLICATIONS

Hoffman et al., "Epidemiology of periodontal disease in poodles," Journal of Small Animal Practice 37:309-316 (1996).

International Search Report mailed Feb. 24, 2020 in International Application No. PCT/US2019/061782.

Kyllar et al., "Morphometric assessment of periodontal tissues in relation to periodontal disease in dogs," J Vet Dent 30:146-149 (2013).

Kyllar et al., "Prevalence of dental disorders in pet dogs," Vet. Med.-Czech, 50(11):496-505 (2005).

Lund et al., "Health status and population characteristics of dogs and cats examined at private veterinary practices in the United States," J Am Vet Med Assoc 214:1336-1341 (1999).

Marshall et al., "A longitudinal assessment of periodontal disease in 52 miniature schnauzers," BMC Veterinary Research, 10:166 (2014).

O'Neill et al., "Prevalence of disorders recorded in dogs attending primary-care veterinary practices in England," PLoS One 9(3):e90501 (2014).

Stella et al., "A cross-sectional study to estimate prevalence of periodontal disease in a population of dogs (*Canis familiaris*) in commercial breeding facilities in Indiana and Illinois," PLoS One, 13(1):e0191395 (2018).

\* cited by examiner

METHOD OR SYSTEM FOR DIAGNOSING PERIODONTAL DISEASE

RELATED APPLICATIONS

This application is a U.S. National Stage Patent Application under 35 U.S.C. § 371 of International Patent Application No. PCT/US2019/061782, filed on Nov. 15, 2019, which claims priority to GB Patent Application No. 1818627.0, filed Nov. 15, 2018, the contents of each of which are hereby incorporated by reference in their entireties, and to which priority is claimed.

FIELD OF THE INVENTION

The present invention relates to methods or systems for determining the susceptibility of a dog to periodontal disease and to the development of treatment regimens based upon the levels of susceptibility determined.

BACKGROUND TO THE INVENTION

Periodontal disease is the most widespread oral disease in dogs. Prevalence estimates of between 44% and to 100% have been reported. The aetiological agent of periodontal disease is dental plaque. The enzymes secreted by plaque bacteria, as well as bacterial antigens, are thought to activate the host inflammatory response initiating the pathogenesis of the disease.

The initial stage of periodontal disease, gingivitis, is clinically observed as red and inflamed gums. In the absence of treatment to remove the plaque biofilm, gingivitis may progress to periodontitis. Periodontitis onset is characterised by destruction of the tissues that support the tooth, such as the periodontal ligament and alveolar bone, the structures that form the periodontium. Early periodontitis is defined as less than 25% attachment loss. In this early stage, the disease can be controlled by professional dental cleanings, to remove plaque and calculus, combined with regular tooth brushing and effective home plaque control programme. However, in the absence of an effective intervention, advanced periodontitis can develop (>50% attachment loss) which is likely to result in chronic pain and ultimately tooth loss.

There is epidemiological evidence to suggest that disease incidence and severity increases with age.

In addition, there have been a small number of studies which associate the prevalence and manifestation of periodontitis to specific breeds of dog. For example, survey of 31,484 dogs examined by veterinary practitioners in private veterinary practices in the USA in 2006 identified the ten purebred dogs most at risk for periodontal disease as toy poodle, Yorkshire terrier, Maltese, Pomeranian, Shetland sheepdog, Cavalier King Charles spaniel, Papillion, standard poodle, dachshund and Havanese (Lund, E. M., Armstrong, P. J., Kirk, C. A., Kolar, L. M., Klausner, J. S. (1999) Health status and population characteristics of dogs and cats examined at private veterinary practices in the United States. J Am Vet Med Assoc 214:1336-1341). A UK study reported the highest prevalence of periodontal disease in Yorkshire terrier (25.2%), followed by cocker spaniel (12.8%), Jack Russel terrier (9.5%), border collie (6.7%), German shepherd dog (4.5%), Labrador retriever (3.2%) and finally Staffordshire bull terrier (2.4%) (O'Neill, D. G., Church, D. B., McGreevy, P. D., Thomson, P. C., Brodbelt, D. C. (2014) Prevalence of disorders recorded in dogs attending primary-care veterinary practices in England. PLoS One 9:e90501).

However, there have been contradictory results. For instance, in a study carried out under anaesthesia or post mortem, the highest level of periodontitis was observed in medium-size breeds (39.5%), followed by large breeds (26.3%), small breeds (20%) and mongrels (14.0%). In terms of breed differences this study reported the highest levels of periodontitis in medium-sized poodle (20%) followed by German shepherd (11.5%), toy poodle (10%), boxer (9%), German hunting dog (8%) and Chihuahua (2%). A study of 123 poodles, aged 2 to more than 12 years, visiting a veterinary practice in Germany reported that 90% of dogs under the age of 4, and 100% of dogs over the age of 4, had at least one tooth affected by periodontitis (Hoffman, Th. & Gaengler, P. (1996) Epidemiology of periodontal disease in poodles. Journal of Small Animal Practice 37:309-316).

Studies have also shown that the gingiva and alveolar bone is significantly thinner in toy breed dogs compared with small and medium-sized breed dogs and that thinner gingiva correlates with an increased incidence of periodontal disease (Kyllar, M., Doskarova, B., Paral, V. (2013) Morphometric assessment of periodontal tissues in relation to periodontal disease in dogs. J Vet Dent 30:146-149).

A higher prevalence, as well as more severe forms, of periodontitis have been noted in smaller breeds of dog in comparison to larger breeds. Marshall et al., BMC Veterinary Research, 2014, 10:166 records a study carried out in miniature schnauzers, who were considered to be an 'at risk' group on the basis of their size.

The applicants have appreciated that a full understanding which particular dogs and teeth are most at risk of developing periodontal disease will enable veterinarians to provide personalised individualised treatment and prevention strategies.

SUMMARY OF THE INVENTION

The applicants have undertaken a retrospective analysis of medical records from a number of US vets. Two studies were undertaken, the objective of the first was to determine the relationship between lifetime prevalence of canine periodontitis or dental calculus and age trends for different breed size categories (extra-small, small, medium-small, medium-large, large and giant). This prompted a second larger study where the objective was to determine associations between the 5-year prevalence of periodontal disease and dental calculus, and breed size category, breed and body weight.

According to a first aspect of the invention there is provided a method for determining the susceptibility of a dog to periodontal disease by
  (i) determining at least two characteristics selected from:
    (a) the breed of the dog;
    (b) the shape of the dog's head;
    (c) the size category of the dog;
    (d) the weight or body condition of the dog;
    (e) the predicted size category or weight of the dog as an adult;
    (f) the age of the dog;
  (ii) comparing the result for each characteristic with a dataset relating to the occurrence of periodontal disease in dogs having similar characteristics; and
  (iii) relating the results from step (ii) in an algorithm to assess the overall susceptibility level.

The method of the first aspect may additionally comprise the step of:

(iv) preparing a customised recommendation for the maintenance of oral health on the basis of the overall susceptibility level.

Where the method comprises step (iv), the method may be for providing a customised recommendation for maintaining oral health of a dog.

The applicants are the first to develop a system for providing a customised recommendation for maintaining the oral health of a particular dog based upon a rationalisation of a variety of risk factors.

The overall susceptibility level determined in step (iii) will suitably provide an indication of whether the dog falls into a high, medium or low risk category for periodontal disease. The number of risk categories may vary depending upon factors such as the number of characteristics determined in step (i) and the sensitivity level available on the basis of the dataset.

As used herein, the term 'dataset' may comprise a table of raw data, such as breed information as listed below in Table 2, but suitably comprises a simplified scoring or weighting scheme which has been derived from the raw data.

The precise nature of the algorithm used in step (iii) above will vary depending upon the particular characteristics used in the method. Typically, a value or 'score' will be attributed to each characteristic, and an algorithm developed on the basis of whether the characteristic contributes more or less to the susceptibility of a dog to periodontal disease.

Characteristics such as weight or age maybe attributed a value directly related to their absolute values such as weight in for example kilograms, or age in years or months. In this case, the lower the weight of the dog, the greater its possible susceptibility to periodontal disease. Thus, weight may be used as a denominator or divisor in the algorithm. However, as periodontal disease is known to increase with age, the age of the dog may be used in a numerator or multiplying factor in any algorithm.

However, for other characteristics, it may be necessary to ascribe a preliminary value or scoring, depending upon the susceptibility level associated with the characteristic.

Thus, for example, it is possible to attribute a value or 'score' to a dog of a particular breed by comparing the breed to a dataset relating to the correlation of breed with periodontal disease as illustrated hereinafter. Some breeds may be highly susceptible to periodontal disease and therefore they will be attributed a high value or score for use in the algorithm.

Values or scores of this nature can also be applied to characteristics such as the shape of the head of the dog. The applicants have found that dogs with a brachycephalic skull (a short length of skull compared to skull width i.e. where the skull width/length ratio expressed as a percentage is at least 80% may be less prone to periodontal disease than those with mesaticephalic skulls (an intermediate length of skull relative to skull width wherein the width/length×100 is between 50-80%), and that those with dolichocephalic skulls (a long length of skull relative to skull width where the skull width/length ratio expressed as a percentage is less than 50%) may be most susceptible to periodontal disease. Thus, a low score of value may be applied to dogs having a brachycephalic skulls, for example a score of 1, whilst higher scores applied to those with either mesaticephalic or diochocephalic skulls, for example scores of 2 and 3 respectively. These scores can then be used in the algorithm as a means of calculating the overall susceptibility.

In a particular embodiment, different algorithms may be applied to different fundamental head shapes. The algorithms may be determined using a dataset obtained from dogs of a particular head shape, as illustrated hereinafter. Data for breeds of dog which are known to be anomalous in their risk levels, for example, dogs of particularly high risk, such as greyhounds, may, if required, be excluded from the dataset used in calculating the algorithm. Where this happens, dogs of that particular breed are suitably excluded from analysis using the specific algorithm. Thus, for example, the risk level for greyhounds will be assessed using parameters other than parameter (b) above, and in particular, will be assessed using parameters (a), (d) and (f) above.

In this case, in a method for determining risk based on an algorithm using parameter (b), may, in a preliminary step determine also (a), and exclude any dog falling within a particular 'excluded' breed from the determination using that algorithm, but instead may divert the dog to the use of a different algorithm.

Similarly, size category of a dog may provide a general indication of its susceptibility to periodontal disease, with dogs is smaller size categories being generally more susceptible to periodontal disease than others. Thus a dataset based upon these findings will suitably provide a 'high risk' value or score for small size category dogs and a 'low-risk' value or score for large dogs.

As used herein, the expression 'size category' refers to the definition of the dog in terms of the average weight of the particular dog breed. Dogs of the same breed have relatively uniform physical characteristics, such as size, coat colour, structure and behaviour. Those traits are developed under controlled conditions by humans. The Fédération Cynologique Internationale currently recognizes 346 pure dog breeds. The breed of a dog can be identified, for example, either by observing its physical traits or by genetic analysis. A pedigree dog is the offspring of two dogs of the same breed, which is eligible for registration with a recognised club or society that maintain a register for dogs of that description. There are a number of pedigree dog registration schemes, of which the Kennel Club is the most well known. Categories are defined as follows in Table 1:

TABLE 1

| Size Category name | Weight range of dog breed |
| --- | --- |
| Toy/Extra small | Up to 6.5 Kg |
| Small | 6.5-9 Kg |
| Medium-small | 9-15 Kg |
| Medium-large | 15-30 Kg |
| Large | 30-40 Kg |
| Giant | Over 40 Kg |

Thus, if a dog's breed is known and clear, then it may be allocated to a particular category and a 'risk factor' allocated to it in the algorithm. For example, a score of 1 may be awarded to giant dogs, 2, for large dogs 3 for medium-large dogs, 4 for medium small dogs, 5 for small dogs and 6 for toy/extra small dogs. In this instance, the score will be used as a numerator in the algorithm. Alternatively the scores may be reversed (i.e. 1 for a toy/extra small dog, 2 for a small dog and so on up to 6 for a giant dog), and the score used in the algorithm as a divisor.

Where weight or size category is utilised as a characteristic of the algorithm, care may need to be taken to ensure that the dog does not belong to any particular large breed which is known to be exceptional in this respect. Therefore, in a particular embodiment, where size category of item (c) is utilised, then breed of item (a) is also taken into account.

In a particular embodiment, characteristic (a) above is a characteristic determined as one of the characteristics used in the method. This is possible where the dog is a pedigree dog. However, the use of this characteristic may be dependent upon the availability of a dataset relating to the occurrence of periodontal disease in dogs of that particular breed.

Where the dog is not a pedigree dog of known breed, or where it is of mixed or unknown breed, then alternative characteristics, which may be readily determined by an examination of the dog, in particular shape of skull and/or weight are suitably employed in the method of the invention.

The precise nature of the characteristics chosen and the algorithm used will therefore vary depending upon the information available about a particular dog. In a particular embodiment, at least three characteristics are chosen to determine the susceptibility level.

A dataset relating to the occurrence of periodontal disease in 60 breeds is summarised in the following Table 2. This table includes data for 60 breeds of dog that most frequently visit a number of US vets.

TABLE 2

| | Periodontal disease | | | | | |
|---|---|---|---|---|---|---|
| Breed size/Breed | Total (95% confidence intervals) | Grade 1 | Grade 2 | Grade 3 | Grade 4 | Dental Calculus (95% confidence intervals) |
| Chihuahua | 20.6% (20.5%-20.8%) | 10.2% | 6.4% | 4.8% | 3.0% | 74.5% (74.4%-74.7%) |
| Maltese | 25.4% (25.2%-25.7%) | 13.0% | 8.5% | 6.1% | 3.6% | 79.7% (79.4%-79.9%) |
| Miniature Pinscher | 22.2% (21.8%-22.6%) | 11.5% | 7.4% | 5.0% | 2.5% | 80.4% (80.0%-80.8%) |
| Miniature Poodle | 28.2% (28.0%-29.1%) | 13.3% | 10.2% | 7.1% | 4.6% | 83.1% (82.6%-83.6%) |
| Papillon | 29.7% (28.9%-30.4%) | 15.2% | 9.7% | 7.5% | 4.1% | 85.4% (84.8%-86.0%) |
| Pekingese | 21.7% (21.1%-22.2%) | 10.2% | 6.9% | 5.1% | 3.5% | 83.0% (82.5%-83.5%) |
| Pomeranian | 26.4% (26.1%-26.7%) | 12.4% | 8.7% | 6.8% | 4.2% | 81.6% (81.3%-81.9%) |
| Shih Tzu | 16.9% (16.7%-17.0%) | 10.2% | 5.1% | 2.8% | 1.5% | 77.0% (76.8%-77.2%) |
| Toy Poodle | 28.9% (28.5%-29.4%) | 13.5% | 10.1% | 7.7% | 4.7% | 82.5% (82.1%-82.9%) |
| Yorkshire Terrier | 25.4% (25.2%-25.6%) | 12.9% | 8.7% | 6.0% | 3.5% | 80.3% (80.1%-80.5%) |
| Bichon Frise | 27.9% (27.5%-28.3%) | 15.0% | 9.5% | 6.3% | 3.3% | 84.5% (84.2%-84.9%) |
| Brussels Griffon | 17.7% (16.4%-19.0%) | 10.9% | 5.2% | 3.2% | 1.3% | 80.2% (78.8%-81.5%) |
| Cairn Terrier | 26.8% (26.0%-27.6%) | 15.1% | 9.7% | 5.6% | 2.4% | 86.4% (85.8%-87.0%) |
| Dachshund | 28.1% (27.9%-28.4%) | 14.0% | 9.3% | 7.0% | 4.2% | 83.2% (83.0%-83.4%) |
| Fox Terrier | 25.6% (24.6%-26.7%) | 13.7% | 8.2% | 5.9% | 3.2% | 84.0% (83.1%-84.8%) |
| Jack Russell Terrier | 22.0% (21.6%-22.3%) | 12.7% | 7.4% | 4.0% | 1.9% | 82.2% (81.9%-82.5%) |
| Lhasa Apso | 22.8% (22.4%-23.3%) | 12.0% | 7.5% | 5.1% | 2.7% | 85.0% (84.6%-85.4%) |
| Miniature Schnauzer | 23.7% (23.3%-24.1%) | 12.2% | 7.5% | 5.5% | 3.3% | 81.9% (81.6%-82.2%) |
| Rat Terrier | 26.0% (25.5%-26.6%) | 14.1% | 8.5% | 5.5% | 3.0% | 84.4% (83.9%-84.8%) |
| West Highland White Terrier | 26.6% (26.0%-27.2%) | 17.0% | 9.2% | 4.2% | 1.6% | 85.9% (85.5%-86.4%) |
| American Cocker Spaniel | 25.3% (24.9%-25.6%) | 13.6% | 9.1% | 5.4% | 2.6% | 84.7% (84.4%-85.0%) |
| American Eskimo | 27.0% (26.2%-27.9%) | 13.5% | 8.8% | 6.6% | 3.6% | 83.8% (83.1%-84.5%) |
| Beagle | 23.2% (22.9%-23.5%) | 13.8% | 7.9% | 4.2% | 1.8% | 82.7% (82.4%-82.9%) |
| Boston Terrier | 13.0% (12.7%-13.3%) | 8.5% | 3.4% | 1.8% | 0.7% | 72.8% (72.3%-73.2%) |
| Cavalier King Charles Spaniel | 27.3% (26.6%-27.9%) | 15.6% | 9.2% | 6.2% | 2.9% | 82.6% (82.1%-83.2%) |
| French Bulldog | 8.3% (7.8%-8.7%) | 6.2% | 1.8% | 0.6% | 0.2% | 61.9% (61.1%-62.7%) |
| Pug | 21.9% (21.6%-22.2%) | 10.9% | 7.4% | 5.3% | 2.8% | 80.4% (80.0%-80.7%) |
| Shetland Sheepdog | 30.6% (29.9%-31.2%) | 16.7% | 10.6% | 6.8% | 3.2% | 87.3% (86.8%-87.7%) |
| Standard Schnauzer | 21.0% (19.3%-22.7%) | 10.5% | 6.7% | 4.9% | 2.5% | 80.5% (78.8%-82.1%) |
| Welsh Corgi | 20.2% (19.6%-20.9%) | 13.1% | 6.2% | 3.2% | 1.0% | 80.7% (80.1%-81.3%) |
| American Staffordshire Terrier | 8.9% (8.4%-9.4%) | 6.9% | 1.9% | 0.6% | 0.2% | 62.9% (62.0%-63.8%) |
| Australian Cattle Dog | 12.6% (12.1%-13.0%) | 8.7% | 3.5% | 1.5% | 0.5% | 71.7% (71.0%-72.3%) |
| Australian Shepherd | 14.3% (14.0%-14.7%) | 10.3% | 4.1% | 1.5% | 0.4% | 73.9% (73.4%-74.3%) |
| Basset Hound | 25.3% (24.7%-26.0%) | 14.5% | 8.8% | 5.0% | 2.0% | 83.1% (82.6%-83.6%) |
| Border Collie | 15.4% (15.0%-15.9%) | 10.1% | 4.5% | 1.8% | 0.9% | 77.6% (77.0%-78.1%) |
| Boxer | 9.0% (8.8%-9.2%) | 6.6% | 2.1% | 0.8% | 0.2% | 63.9% (63.6%-64.2%) |
| English Bulldog | 7.3% (7.0%-7.5%) | 5.4% | 1.5% | 0.6% | 0.2% | 58.6% (58.2%-59.1%) |
| Pit Bull | 4.8% (4.7%-4.9%) | 3.9% | 1.0% | 0.2% | 0.1% | 49.3% (49.1%-49.5%) |
| Siberian Husky | 10.0% (9.5%-10.4%) | 7.5% | 2.4% | 0.8% | 0.3% | 65.4% (64.7%-66.1%) |
| Standard Poodle | 16.9% (16.1%-17.6%) | 11.1% | 5.3% | 2.1% | 0.8% | 79.0% (78.1%-79.8%) |
| Akita | 11.4% (10.7%-12.2%) | 7.9% | 3.5% | 1.3% | 0.2% | 71.0% (69.9%-72.0%) |
| Alaskan Malamute | 11.7% (10.7% -12.6%) | 8.3% | 3.3% | 1.1% | 0.3% | 72.3% (71.0%-73.6%) |
| American Bulldog | 6.1% (5.8%-6.4%) | 4.8% | 1.3% | 0.3% | 0.1% | 56.4% (55.8%-57.1%) |
| Doberman Pinscher | 10.1% (9.7%-10.6%) | 7.3% | 2.6% | 0.8% | 0.3% | 66.8% (66.0%-67.5%) |
| German Shepherd | 8.1% (8.0%-8.3%) | 5.9% | 2.1% | 0.6% | 0.2% | 61.0% (60.7%-61.3%) |
| Golden Retriever | 13.8% (13.6%-14.0%) | 10.0% | 3.9% | 1.2% | 0.3% | 77.7% (77.4%-78.0%) |
| Greyhound | 38.7% (37.4%-39.9%) | 17.1% | 12.3% | 11.9% | 6.4% | 89.2% (88.4%-90.0%) |
| Labrador Retriever | 12.6% (12.5%-12.8%) | 9.2% | 3.5% | 1.1% | 0.3% | 73.7% (73.5%-73.8%) |
| Rhodesian Ridgeback | 13.1% (12.1%-14.0%) | 8.8% | 4.0% | 1.2% | 0.4% | 71.9% (70.6%-73.2%) |
| Weimaraner | 14.3% (13.7%-14.9%) | 10.4% | 4.2% | 1.3% | 0.3% | 75.7% (75.0%-76.4%) |
| Bernese Mountain Dog | 15.5% (14.3%-16.7%) | 11.2% | 5.5% | 1.3% | 0.2% | 73.9% (72.5%-75.3%) |
| Bloodhound | 9.3% (8.1%-10.6%) | 6.3% | 2.7% | 0.9% | 0.5% | 66.7% (64.6%-68.7%) |
| Bullmastiff | 7.0% (6.1%-7.9%) | 5.8% | 1.6% | 0.4% | 0.1% | 61.6% (59.8%-63.3%) |
| Cane Corso | 4.0% (3.4%-4.5%) | 3.4% | 0.6% | 0.2% | 0.0% | 42.9% (41.4%-44.4%) |
| Great Dane | 10.5% (10.1%-10.9%) | 7.7% | 2.8% | 0.8% | 0.2% | 63.0% (62.4%-63.7%) |
| Great Pyrenees | 11.4% (10.6%-12.2%) | 8.5% | 2.8% | 1.1% | 0.2% | 69.7% (68.6%-70.9%) |

TABLE 2-continued

| | Periodontal disease | | | | | |
|---|---|---|---|---|---|---|
| Breed size/Breed | Total (95% confidence intervals) | Grade 1 | Grade 2 | Grade 3 | Grade 4 | Dental Calculus (95% confidence intervals) |
| Newfoundland | 8.8% (7.8%-9.8%) | 6.8% | 2.4% | 0.5% | 0.1% | 71.2% (69.6%-72.8%) |
| Presa Canaria | 4.8% (3.6%-6.0%) | 3.9% | 0.8% | 0.2% | 0.2% | 49.6% (46.8%-52.4%) |
| Rottweiler | 7.8% (7.5%-8.0%) | 5.4% | 2.2% | 0.7% | 0.2% | 63.3% (62.8%-63.8%) |
| Saint Bernard | 11.2% (10.5%-12.0%) | 8.0% | 3.4% | 0.9% | 0.2% | 69.1% (68.0%-70.2%) |

Such a dataset may give rise to a parameter which may be used in the algorithm to determine the susceptibility level. For example, in the above table, where the percentage total of the dogs showing periodontal disease is in excess of 20%, a score of 3 may be allocated in the algorithm applied to dogs of that particular breed. A score of 2 may be awarded in the algorithm to a dog whose breed shows between 10-20% periodontal disease, and a score of 1 may be awarded to a dog whose breed shows periodontal disease in less than 10% of total population. Additional levels may be introduced into the algorithm. For example, breeds showing high levels of periodontal disease, for example in excess of 28 or 30% or 35% of the total population may be awarded higher scores, for example of 4, 5 or 6. Such a score may be referred to as a breed score 'B'.

In a particular embodiment, an algorithm will combine a breed characteristic of 'B' score with the age characteristic, which is designated as 'A' where A represents the dogs age in for example years. Thus, in the case of a pedigree dog, a starting point for the algorithm may comprise an equation as follows:

$$R_p = B \times A$$

Where $R_p$ is the risk parameter and B and A are as defined above.

It is also clear that being of non-standard size for the breed, in particular, where dogs are overweight or underweight for the breed type, or have a poor overall body condition, suffer an increased risk of periodontal disease. Therefore, in a particular embodiment, the weight of the dog is determined and this is compared to the acceptable weight range for the breed. If there is a significant discrepancy, for example greater than 1 Kg, 2 Kg, 3 Kg, 4 Kg, 5 Kg, 6 kg or more, an additional weighting factor may be included in the algorithm. For example, the above equation may be modified by a factor (1+DW/W), where W is the healthy body weight of the dog and DW is the number of kilograms over or under weight that the dog may be.

In an alternative, the body condition score is determined for the particular dog and this is used to provide the additional weighting factor. Body condition scores are well known and understood in the veterinary arena and may be determined by an examination of the dog to determine factors such as whether or not the ribs are palapable, whether a waist is detectable when viewed from above or the side, and whether an abdomen is tucked up when viewed from the side. The particular factors will vary depending upon the breed type.

For example, the WSAVA (The World Small Animal Veterinary Association) provides a body condition score index summarised in the following Table 3.

TABLE 3

| Body Condition Score | Description of characteristics |
|---|---|
| 1 | Ribs, lumbar vertebrae, pelvic bones and all bony prominences evident from a distance. No discernible body fat. Obvious loss of muscle mass. |
| 2 | Ribs, lumbar vertebrae and pelvic bones easily visible. No palpable fat. Some evidence of other bony prominences. Minimal loss of muscle mass. |
| 3 | Ribs easily palpated and may be visible with no palpable fat. Tops of lumbar vertebrae visible. Pelvic bones becoming prominent. Obvious waist and abdominal tuck. |
| 4 | Ribs easily palpable, with minimal fat covering. Waist easily noted, viewed from above. Abdominal tuck evident. |
| 5 | Ribs palpable without excess fat covering. Waist observed behind ribs when viewed from above. Abdomen tucked up when viewed from side. |
| 6 | Ribs palpable with slight excess fat covering. Waist is discernible viewed from above but is not prominent. Abdominal tuck apparent. |
| 7 | Ribs palpable with difficulty; heavy fat cover. Noticeable fat deposits over lumbar area and base of tail. Waist absent or barely visible. Abdominal tuck may be present. |
| 8 | Ribs not palpable under very heavy fat cover, or palpable only with significant pressure. Heavy fat deposits over lumbar area and base of tail. Waist absent. No abdominal tuck. Obvious abdominal distention may be present. |
| 9 | Massive fat deposits over thorax, spine and base of tail. Waist and abdominal tuck absent. Fat deposits on neck and limbs. Obvious abdominal distention. |

However, under this system a dog at an ideal or acceptable weight and body shape for the breed is awarded a body condition score of 4 or 5. However, poor body conditions scores of 1-3 are awarded where an animal is significantly underweight and in poor emaciated condition, whereas a body condition score in the range of from 7 to 9 is awarded to overweight and under exercised dogs. Thus in this case, a weighting factor may be based upon a particular body condition score C. The weighting factor may for example be the difference between actual body score C and 4.5, expressed as a positive number.

Thus a refinement of the above algorithm may be represented by the equation:

$$R_p = (B \times A)(1 + Q/10)$$

where $R_p$, B, A are as defined above, and 'Q' is defined as a weighing factor.

If the breed of a particular dog is unknown or uncertain, for example because the dog is of a mixed breed, characteristics (a), (c) and (e) above may not be a suitable parameter to utilise. In this case however, an alternative method will rely on the use of factors (b) the shape of the dog's head, (d) the weight of the dog and/or (f) the age of the dog.

In a particular embodiment of the invention, the method allows for a quantitative level of susceptibility to periodontal disease to be determined for a particular dog using characteristics of the dog which can readily be determined. In particular, a method is provided to quantify the risk of periodontal disease using measurements of bodyweight, age and skull shape.

As discussed above, it is well known that domestic dogs may be broadly categorised into three skull shapes. Brachycephalic dogs (for example pugs, boxers and bulldogs) generally have a short length of skull, relative to the skull width. Dolichocephalic dogs (for example greyhounds, whippets and Shetland sheepdogs) have a particularly long length of skull relative to the skull width. Mesaticephalic dogs (for example Labrador retrievers and golden retrievers) have an intermediate length of skull relative to the skull width.

The applicants have found from an analysis of a broad range of data from many breeds as explained more fully below, that there is a correlation between prevalence of periodontal disease and skull shape, when taking account of age and body weight of the dog. In particular, the applicants have found that, for most dogs, a reliable risk parameter can be calculated on the basis of the following equation.

$$R_p = (A * S)/W \quad \text{Equation (1)}$$

where A is the age of the dog, in particular in years, S is the quantification of skull shape, and W is the weight of the dog for example in kilograms.

The "Risk Level Factor" (represented by symbol 'L') can then be calculated in accordance with equation (2) below.

$$L = 0.0662 * LN(R_p) + 0.2137 \quad \text{Equation (2)}$$

Here 'LN' is the natural logarithm.

It is then possible to prepare a risk level table to fit the results. The precise figures in this table will vary depending upon the units of age and weight used as well as the figure ascribed to the various skull shapes.

For example, in a particular embodiment, values are assigned to dog skull types as follows.

TABLE 4

Quantification of Skull Shape

Brachycephalic skull: 1.0
Mesaticephalic skull: 2.0
Dolichocephalic skull: 3.0

In order to determine the quantitative level of risk, three characteristics of the dog must be determined:
The age of the dog in years (A)
The body weight of the dog in kilograms (W).
The skull shape (S).

Using these figures, a risk level can then be assign as shown in Table 5 below, and the appropriate level of intervention can be estimated accordingly.

TABLE 5

Risk Level

L < 0.10: LOW risk
0.10 < L <0.15: LOW-MEDIUM risk
0.15 < L < 0.20: MEDIUM risk.
0.20 < L < 0.30: MEDIUM-HIGH risk.
L > 0.30: HIGH RISK Examples of the application of this particular algorithm are provided hereinafter.

However, the applicants have also found that within particular head shapes, specific algorithms may be developed which are particularly suitable. Thus, in a particular embodiment, the shape of the dog's head is measured, and this is then used to select the particular algorithm to be applied.

For brachycephalic dogs, particularly useful models are represented by the following equations:

$$\text{Prevalence} = 0.0073 * (Age)^{1.74} + 43.1 * (Weight)^{-0.98} \quad \text{Equation (3A)}$$

$$\text{Prevalence} = (42.05701 \times (Weight)^{-0.96292}) + (0.006648 \times (Age)^{1.775244}) \quad \text{Equation (3B)}$$

Age here is expressed in months and weight in kg, but the equation may be adapted for different units of the various parameters, for example to adjust the model to consider age in years, rather than months, if required. FIG. 9 shows actual values of prevalence plotted against values predicted from the equation 3B above. The $R^2$ value of more than 0.99 clearly indicates a very good fit.

Similarly, for mesocephalic dogs, a suitable algorithm would be represented by Equation 4:

$$\text{Prevalence} = (40.80988 \times (Weight)^{-0.46702}) + (0.000222 \times (Age)^{2.460098}) \quad \text{Equation (4)}$$

Dolichocephalic dogs (excluding greyhounds) may suitably be assessed using an algorithm incorporating Equation 5.

$$\text{Prevalence} = (320.2686 \times (Weight)^{-2.55114}) + (0.021566 \times (Age)^{1.624599}) \quad \text{Equation (5)}$$

In the case of dogs of unknown breed, an optional additional step may be to determine some breed information using genetic analysis, for example, using the Canine Genetic Analysis™ DNA Test, available from the Banfield Pet Hospital®. This will allow the identification of breed makeup back to the great-grandparents to be determined, based upon a comprehensive analysis of multiple genes. If the dog has a parent or grandparent known to be in a 'high risk' category, this could be incorporated as a weighting factor into the algorithm used.

In a particular embodiment of the invention, the size category of the dog is used to provide a factor in the algorithm used to calculate susceptibility levels. As discussed above, the dog may be allocated to the toy, small, medium, large or giant on the basis of its breed, and a risk factor allocated on the basis of this category. In particular, the risk factors are higher, the smaller the dog. However, it has been recognised that for some breeds, in particular greyhounds or basset hounds, this generalised approach may not be adequate and that therefore the breed information would be preferable.

Furthermore, as being over-weight or under-weight for the breed type or being out of condition increases the risk of periodontal disease, then even where the breed and therefore the category of the dog is known, weighing the particular dog or determining its body condition is worthwhile to determine whether an additional weighting of risk factor should be added to the algorithm in order to take account of the additional risk associated with this factor, as discussed above. In this context, body condition may be determined using conventional criteria as discussed above.

In a particular embodiment, therefore, the method of the invention involves a preliminary step of determining the weight of an adult dog by weighing the dog. This may be used to allocate the dog to a particular weight category as discussed above or it may be used to determine whether the dog is at increased risk as a result of it being outside the weight category for the particular breed. In that case, the risk factor may be increased, for example, as described above.

In another embodiment, the method of the invention involves a preliminary step of determining the body condition of a dog as defined above, by assessment using the criteria listed above.

Where the dog is young and has not reached its mature weight, an assessment of the predicted size category or weight of the dog as an adult may be carried out to determine characteristic (e) above. Where the dog is a pedigree dog, the size category or weight may be readily determined on the basis of the breed type. However, for mixed breed dogs, an assessment may be carried out using available assessment systems such as the WISDOM™ Panel Canine DNA test.

Another factor which may influence the susceptibility of a particular dog to periodontal disease is age. Therefore, in a particular embodiment, the age of the dog is also determined in step (i) and the age results are compared with a dataset relating to the occurrence of periodontal disease in dogs of a similar age as well as a similar breed and size.

Alternatively, the age of the dog may be given a particular 'weighting' in the algorithm, for example, as illustrated above. As a result, older dogs may be given a more stringent regime in the customised recommendation.

The applicants have also found that periodontal disease may occur in particular types of teeth, depending upon the breed, as set out below. This may assist in allowing a veterinarian or owner to focus attention and effort in a particular area of a dog's mouth, in particular when monitoring the onset of periodontal disease.

The customised recommendation will comprise dental health care programmes of varying degrees of stringency and will be determined on the basis of the analysis carried out as described above.

In accordance with the method of the invention, the customized recommendation may comprise at least one of the following:
(a) a recommendation regarding frequency of review of periodontal health;
(b) a recommendation regarding nature and frequency of feeding of products which assist dental health or hygiene;
(c) a recommendation regarding application or frequency of tooth brushing;
(d) a recommendation regarding the size and/or nature of tooth cleaning products; and
(e) a recommendation regarding the application or frequency of clinical interventions such as deep cleaning procedures carried out by a veterinarian, if necessary under anesthetic.

In this context, recommendations regarding the frequency of review of periodontal health will typically be in the range of from 3 months to 2 years depending upon the level of risk the particular dog is susceptible to. Thus, dogs deemed to be a 'high risk' of periodontal disease using the algorithm may be recommended for dental checks to be carried out every 3-6 months, to allow the occurrence of dental disease to be identified at an earlier stage, so that veterinary intervention, can be instigated when necessary with minimum delay. Alternatively, owners may be recommended to carry out visual inspections of their dog's teeth at regular intervals to check for inflammation, gingival recession, furcation exposure (exposure of the roots of the tooth), mobile/missing teeth and excessive plaque/calculus.

Dogs identified using the method of the invention as being at 'low' or 'medium' risk may be subjected to dental review less frequently, for example during an annual veterinary check.

The review process may comprise, for example, a bacteria or enzyme (e.g. protease) test of swabs taken from the mouth of a dog. This may be taken from specific teeth types identified using the method of the invention as being at particular risk in the dog under test.

The results of any review process may be fed back in a feedback loop in the method of the invention, so that if for example, the susceptibility of a particular dog has been increased as a result of the onset of some disease, this information is taken into account in adjusting the customised recommendation. Similarly, if a dog is determined to have better than expected dental health in the course of a review, the customised recommendation may be adjusted to a less stringent regimen.

The customised recommendations may include suggestions for the use of a 'dental diet' as the main meal, oral solutions, or the administration of particular products which are believed to assist or promote dental health or hygiene, such as Dentastix® or Greenies™, or of chew toys which are known to impede plaque or calculus accumulation.

Dental diets are generally in the form of kibbles and are available commercially. They may have reduced protein and calcium content which limits mineralisation of plaque and tartar. They may also include increased fibre which holds the kibble together for longer which then cleans the surface of the tooth. Furthermore, the size of the kibble may be selected so that it engulfs the tooth before it splits enabling the fibres to exert a gentle abrasive effect to wipe the surface of the tooth clean.

The dental diets may include additional ingredients, such as sodium polyphosphate, which binds with calcium in saliva, thus making it unavailable for the formation of tartar, zinc which helps to slow down tartar build-up and has antiseptic properties, therefore, reducing bad breath and green tea polyphenols help to maintain a healthy mouth and gums.

Oral solutions or dental rinses may be in the form of solutions to add to a dog's water bowl, or sprays or gels for application directly into the mouth of the dog. These may contain for example antimicrobial compounds such as chlorhexidine gluconate.

Other products such as Dentastix® or Greenies™ are available for dogs of different sizes, and they may be recommended for daily use in the case of dogs identified as being at 'high risk', and/or at less frequent intervals for others.

Other interventions that may be included in the customised recommendation include tooth brushing or even a deep cleaning procedure, which may be carried out under anaesthetic. This is a fairly extreme intervention which dog owners may not utilise themselves, at least not on a regular basis. However, it may be suggested that this is undertaken on a regular basis.

During their lifetimes, the susceptibility of a dog to periodontal disease will generally increase, and therefore the customised recommendation may change over time. In accordance with the method of the invention, an owner may be provided with advice or information regarding the rate of increase of risk over time and any changes that may be consequent in terms of the customised recommendation and adequate treatment regime that will occur.

Thus, examples of customised recommendations are summarised in the following Table 6:

TABLE 6

| Dog identified as being at high risk in accordance with the method of the invention | Dog identified as being at medium risk in accordance with the method of the invention | Dog identified as being at low risk in accordance with the method of the invention |
|---|---|---|
| Check every 3 months Provide recommendation for use of products such as Dentastix/Greenies on a daily basis. Suggest strict adherence to daily tooth brushing regime | Provide recommendation for use of products such as Dentastix/Greenies on a twice weekly basis. Retest in 3, 4, 5 or 6 months Suggest good adherence to daily tooth brushing regime | Basic care recommended and education/information on increasing risk with age/breed provided: Retest in 6-12 months Suggest daily tooth brushing regime |

The method may comprise the step of carrying out the customised recommendation.

In a further aspect the invention provides the method of the first aspect of the invention, carried out by a computer.

Also provided is a data-processing apparatus or device or system comprising means for carrying out the steps of the method of the first aspect of the invention.

Further provided is a computer program product comprising instructions which, when the program is executed by a computer, cause the computer to carry out the method of the first aspect of the invention. The invention also provides a non-transitory computer readable medium having the program stored thereon.

Thus, the invention further provides a system for providing a customized recommendation for a treatment regimen for maintaining oral health of a dog, said system comprising:
 a processor; and
 a memory that stores code of an algorithm that, when executed by the processor,
 causes the computer system to receive at least a first and a second input wherein
 the first and second inputs are characteristics selected from
  (a) the breed of the dog;
  (b) the shape of the dog's head;
  (c) the size category of the dog;
  (d) the weight or the body condition of the dog;
  (e) the predicted size category or weight of the dog as an adult;
  (f) the age of the dog;
 analyze and transform the first and/or second inputs to derive a categorization of the susceptibility of the dog to periodontal disease via an algorithm, wherein the algorithm comprises code developed from at least one training dataset, the training dataset comprising information relating to the occurrence of periodontal disease in a set of sample animals having the said characteristics;
 generating an output, wherein the output is the categorization of the susceptibility of the dog to periodontal disease;
 provide a customized recommendation based on output for an oral health regimen of the dog; and
 display the categorization or customized recommendation on a graphical user interface.

In a particular embodiment, the algorithm causes the processor to compare the weight of the dog to the expected weight for the breed, or the body condition of the dog, and takes account of whether the dog is over or under weight or has a poor body condition in making the customized recommendation.

In another particular embodiment, the algorithm stores code that, when executed, causes the computer system to receive a first input which is information relating to the shape of the dog's head, a second input which is the weight of the dog and a third input which is the age of the dog, analyse and transform the first, second and third inputs to derive the categorization of the susceptibility of the dog to periodontal disease via the classification algorithm. In particular, the algorithm uses the equations (1) and (2) or (3A) or (3B) above.

In another particular embodiment, the algorithm stores code that, when executed, causes the computer system to receive a fourth input comprising the results of a dental review carried out on the dog, and where said fourth is analysed and transformed along with the first and/or second and/or third inputs to derive the categorization of the susceptibility of the dog to periodontal disease via the classification algorithm. This provides a useful 'feedback' loop so that dogs who fall outside the normal range for the breed in terms of particularly good or poor dental health may have the customized recommendation adjusted accordingly.

Such a review may comprise the results of an analysis of a mouth swab from the dog. The analysis may be for any appropriate diagnostic, such as bacterial and host derived proteins, such as enzymes, that indicate the presence of or susceptibility to periodontal disease. As described above, the swab taken may be from specific teeth types, which have been found to be particularly susceptible.

A non-transitory computer-readable medium for use in the system described above and storing instructions that, when executed by a processor, cause a computer system to determine or provide a customized recommendation for a treatment regimen for maintaining oral health of a dog in accordance with the method of the invention forms a further aspect of the invention.

In yet a further aspect of the invention there is provided a method for reducing a risk of developing periodontal disease in a dog comprising: determining an overall susceptibility of the dog to the periodontal disease on the basis of at least two characteristics selected from
  (a) the breed of the dog;
  (b) the shape of the dog's head;
  (c) the size category of the dog;
  (d) the weight or body condition of the dog;
  (e) the predicted size category or weight of the dog as an adult;
  (f) the age of the dog;
and providing dental monitoring and treatment for the dog based on the overall level of susceptibility.

Suitable dental treatment and monitoring regimens are as described above.

If required, the training dataset used in the systems and methods described above may be filtered by a set of inclusion and/or exclusion criteria. Certainly, animals may be excluded from the dataset if required, for example on the basis of health or lack of information on breed or health, as illustrated for example below.

A retrospective analysis of clinical data from over 900 primary care veterinary clinics in the USA showed that the lifetime prevalence of periodontitis and dental calculus differed according to breed size category. This study showed that extra-small breeds of dog had the highest lifetime prevalence followed by small and then medium-small breed size groups whereas medium-large, large and giant breed size groups had the lowest. Extra-small dogs also had the highest prevalence of dental calculus up to about eight years of age but the giant breed group had the highest lifetime prevalence above this age. Subsequent regression analysis of the top 10 breeds for each breed size category confirmed these findings in that the odds of periodontal disease increased with breed size category.

The extra-small dog size category had a significantly higher probability of periodontal disease than all other groups. The small breed size categories had the next highest probability of periodontal disease followed by the medium-small breed size category, and both were significantly different than all other breed size categories and each other. The medium-large, large and giant breed size categories were not significantly different from each other. With respect to dental calculus extra-small and small breed dogs had a significantly higher probability of dental calculus than the other size categories and medium-large breeds had a significantly lower probability than the other breed size categories. These findings are supported by a number of other studies which have reported that periodontal disease is more frequent in small dogs compared to larger dogs. The trends for dental calculus with breed size category were less obvious as has been reported in other studies. These differences in risk of periodontal disease amongst the various size categories might be explained by genetics. Indeed, clinical and scientific data have indicated that there is significant genetic influence on human periodontal disease. A study of human monozygotic twins estimated that adults with chronic periodontitis had a 50% hereditability rate, which suggests that about half of the variation of the disease within a population is due to genetic factors.

The applicants have found that certain breeds have a genetic predisposition to periodontal disease, possibly due to differences in their immune response, that make the gingiva more susceptible to periodontal disease. Alternatively, it has been hypothesised that breed size differences could be due to the same degree of bone loss having a greater clinical effect in small dogs compared to larger dogs. Small dogs have a higher ratio of tooth size to jaw size than large dogs and therefore, with less bone supporting the tooth, mobility and furcation exposure occurs more rapidly.

Investigation of the overall 5-year period prevalence of periodontal disease and dental calculus across 60 breeds of dog showed that the prevalence of periodontal disease was 18.2%, and the prevalence of dental calculus was much higher at 74.5%.

The majority of the 20 breeds most frequently diagnosed with periodontal disease were in the three smallest breed size groups. Seventeen of these breeds also had the highest probability of dental calculus.

The breed regression models confirmed the findings that within the extra-small breed size category Yorkshire terriers, Maltese, miniature poodles, papillon, pomeranian, and toy poodle had the highest odds of periodontal disease. Although differences between breeds were not as marked, these six breeds were also among those with the highest odds of dental calculus along with Pekingese. In the small breed size category, dachshunds had the highest probability of periodontal disease but were not significantly different from Brussels griffon, Cairn terrier, fox terrier, rat terrier and West Highland white terrier. Small breeds were generally very similar in their odds of dental calculus diagnosis with the exception that West Highland white terriers had a significantly increased probability of dental calculus compared to Jack Russell terriers and dachshunds. In the medium-small breed size category cavalier King Charles spaniels had the highest probability of periodontal disease but this was not significantly different from American Eskimo, Shetland sheep dogs and standard schnauzers. These breeds also had the highest odds of dental calculus along with American cocker spaniel, beagle and Welsh corgi. There are only a small number of studies that compare the prevalence of periodontal disease and dental calculus across breeds. Data from 235 purebred dogs support the findings of this study in that periodontitis was more frequently identified in small breeds and especially in poodles. An investigation of 162 dogs, aged between 7 months and 14 years, observed periodontitis most frequently in toy/miniature poodles and dachshunds but infrequently in German shepherd dogs. Furthermore, a study of 123 poodles (size category not defined) showed that 90% of dogs under four years of age and all dogs older than four years had at least one tooth with periodontitis. A longitudinal assessment of 52 miniature schnauzers showed that 98% developed some level of periodontitis within 30 weeks of stopping tooth brushing. Clinical attachment loss (≥1 mm) was observed in 20% of one year old beagles, increasing to 84% of dogs aged more than three years, and deeper probing depths (≥4 mm) were observed in up to 81% of dogs depending on age.

In the medium-large breed size category basset hounds had the highest probability of periodontal disease but was not significantly different from the standard poodle. These breeds also had the highest odds of dental calculus, along with Australian shepherd and border collie. The most striking finding was that of the large breeds, where greyhounds had a significantly higher probability of periodontal disease than all other breeds in this size category. Greyhounds also had the highest odds of dental calculus along with Akita, Alaskan malamute, Rhodesian ridgeback and Weimeraner. It is likely that many of the greyhounds in the U.S. pet population are retired racing greyhounds, and dental care was probably not a main concern prior to retirement. It is also likely that genetics and environmental factors play a role. Most greyhound trainers feed their own diets, predominantly raw meat, which is not a balanced food and is deficient in vitamins and minerals It has also been reported that Italian greyhounds have a simple recessive mutation associated with amelogenesis imperfecta, a disorder of the tooth which is manifested by enamel roughening/thinning. It is therefore possible that this enamel defect may favour the development of dental plaque and could partly explain the high prevalence of periodontal disease. Further studies in different breeds of dog are required to determine whether genetic or environmental factors have the greatest influence on periodontal disease and dental calculus.

The applicants identified a number of risk factors for periodontal disease and dental calculus, in addition to breed and breed size category. The mean lifetime prevalence of periodontitis increased with age across all breed size categories. This finding agrees with a number of other studies that have shown that the incidence and severity of periodontal disease significantly increases with increasing age. Likewise the applicants found that the lifetime prevalence for dental calculus increased with age across all breed size categories. Again this is supported by a number of published studies where the amount of calculus deposition has also been shown to significantly increase with age. The breed size category and some of the breed regression models showed that there was a significant effect of age on the odds of periodontal disease and dental calculus diagnosis, although the odds were small. This suggests that the relative impact of age on the odds of developing periodontal disease and calculus is not markedly different across the various breeds or breed size categories The breed size categories and breed regression models showed that dogs classified as overweight had significantly increased odds of periodontal disease and dental calculus diagnosis. With respect to underweight dogs, only the extra-small and giant breeds had increased probability of periodontal disease diagnosis, but all regression models showed that being underweight increased the probability of dental calculus. The increased probability of periodontal disease and dental calculus in underweight and overweight dogs is possibly because they are less likely to receive an effective dental care regime (e.g. tooth brushing, dental treats, dental prophylaxis). It is also plausible that they are those with more serious disease conditions that may be linked to periodontal disease although this was not investigated in this study: This may make dental cleaning a lower priority in patient care or even not recommended (i.e., higher risk for general anaesthesia). This finding concurs with studies of humans that have shown individuals who were overweight or obese have a higher susceptibility to developing periodontal disease. A systematic review of longitudinal and experimental studies suggested that being overweight, obesity, weight gain, and increased waist circumference may be risk factors for the development and progression of periodontitis. These studies, however, concluded that the results originated from limited evidence and that more longitudinal studies are required.

Most surprisingly, the applicants have found by analysing the data that there is a clear correlation with head shape and periodontal disease that this may also be used as a factor when determining susceptibility.

The applicants have carried out a study provides new insights into breed differences in the risk of periodontal disease and calculus deposition. It shows that there is a strong relationship between breed size category and lifetime prevalence of periodontal disease and to a lesser extent dental calculus. In general, the smaller the breed, the higher the odds of periodontal disease and, at most ages, calculus diagnosis. It also supports previous reports that some breeds of dog are more predisposed to these oral conditions than other breeds. Veterinarians should therefore focus their client education and diagnostic efforts on the breed size categories and breeds at highest risk of developing periodontal disease and dental calculus. This targeting would improve their effectiveness of providing quality care to their patients, both inside the hospital and at home. It has been shown that by eliminating calculus and then subjecting dogs to daily repeated and careful tooth brushing, it is possible to establish and maintain healthy gingiva. However, this is not always practical, and the challenge therefore is to find ways to retard or prevent plaque accumulation that are practical for dogs and their owners.

A further aspect of the invention provides a method for determining the susceptibility of a dog to periodontal disease comprising the steps of:
(i) comparing at least one characteristic determined about the dog, selected from:
(a) the breed of the dog;
(b) the shape of the dog's head; and
(c) the size category of the dog or the predicted size category or weight of the dog as an adult;
with a dataset relating to the occurrence of periodontal disease in dogs having that characteristic to determine a risk value related to susceptibility.

Step (i) preferably comprises comparing two or three characteristics determined about the dog, selected from
(a) the breed of the dog;
(b) the shape of the dog's head; and
(c) the size category of the dog or the predicted size category or weight of the dog as an adult; with two or more datasets.

The method preferably further comprises comparing at least one or both characteristics determined about the dog, selected from the weight or body condition of the dog; and the age of the dog with a dataset relating to the occurrence of periodontal disease in dogs having similar characteristics.

When more than one characteristic is used, the characteristics selected may be any combination of the characteristics mentioned, for example, those combinations shown in the rows of table 7.

TABLE 7

| | | | | |
|---|---|---|---|---|
| breed | Head shape | | | |
| breed | | Size category or predicted size category | | |
| breed | | | Weight or body condition | |
| breed | | | | Age |
| breed | Head shape | Size category or predicted size category | | |
| Breed | Head shape | | Weight or body condition | |
| Breed | Head shape | | | Age |
| breed | | Size category or predicted size category | Weight or body condition | |
| breed | | Size category or predicted size category | | Age |
| breed | | | Weight or body condition | Age |
| breed | Head shape | Size category or predicted size category | Weight or body condition | |
| breed | Head shape | Size category or predicted size category | | Age |
| breed | Head shape | | Weight or body condition | breed |
| breed | | Size category or predicted size category | Weight or body condition | Age |
| breed | Head shape | Size category or predicted size category | Weight or body condition | Age |
| | Head shape | Size category or predicted size category | | |
| | Head shape | | Weight or body condition | |
| | Head shape | | | Age |
| | Head shape | Size category or predicted size category | Weight or body condition | |

TABLE 7-continued

| Head shape | Size category or predicted size category | Weight or body condition | Age |
|---|---|---|---|
| Head shape | | | Age |
| Head shape | | Weight or body condition | Age |
| | Size category or predicted size category | Weight or body condition | |
| | Size category or predicted size category | | Age |
| | Size category or predicted size category | Weight or body condition | Age |
| | | Weight or body condition | Age |

For the avoidance of doubt, the characteristics may be combined as shown in the table, when used in any of the aspects of the invention.

The method may also comprise determining any of the characteristics.

Where the method comprises determining more than one characteristic, it may also comprise combining the risk values obtained from step (ii) to assess overall the overall susceptibility level. The characteristics may be combined in an algorithm, as in other aspects of the invention. The algorithm may be carried out using a computer. Computer programs, systems and data carriers, as described in other aspects are also provided.

The method may comprise the step of providing a customised recommendation for the dog, as in other aspects of the invention. For example, the invention provides a method for reducing a risk of developing periodontal disease in a dog comprising assessing susceptibility of the dog to periodontal disease as described and providing dental monitoring and treatment.

According to certain non-limiting embodiments, a method can be performed by a computer for determining susceptibility of a dog to periodontal disease. The method can comprise determining a characteristic of the dog selected from at least one of: (a) a breed of the dog, (b) a shape of the dog's head, (c) a size category of the dog, (d) a weight or body condition of the dog, (e) a predicted size category or weight of the dog as an adult, or (f) an age of the dog. The method can also comprise comparing the characteristic with a dataset comprising an occurrence of the periodontal disease in other dogs having the at least one characteristic, and/or detecting an overall susceptibility level of the dog for the periodontal disease. In addition, the method can also include displaying a customized recommendation on a graphical user interface of the computer based on the overall susceptibility level of the dog.

The customized recommendation comprises recommendation for maintaining oral health of the dog. The method can comprise preparing the customized recommendation for the maintenance of oral health on the basis of the overall susceptibility level. In addition, or as an alternative to, the method can also comprise determining the breed of the dog.

In certain non-limiting embodiments the detecting can comprise using an algorithm to assess the overall susceptibility level of the dog for the periodontal disease. In some embodiments in which the selected characteristic of the dog is the shape of the dog's head, a different algorithm can be applied based on whether the dog has a brachycephalic, a mesaticephalic, or a dolichocephalic skull. In certain non-limiting embodiments, the algorithm comprises a first equation represented by $Rp=(A*S)/W$, where A is the age of the dog in years, S is a quantification of a skull shape on the dog, W is the weight of the dog, and Rp is a risk parameter of the dog. In certain non-limiting embodiments, a Risk Level Factor, represented by symbol L is calculated in accordance with a second equation $L=0.0662*LN(Rp)+0.2137$, where LN is a natural logarithm.

In certain non-limiting embodiments, the customized recommendation comprises at least one of the following: (a) a recommendation regarding frequency of review of periodontal health; (b) a recommendation regarding nature and frequency of feeding of products which assist dental health or hygiene; (c) a recommendation regarding application or frequency of tooth brushing; (d) a recommendation regarding a size or nature of tooth cleaning products; and (e) a recommendation regarding an application or frequency of clinical interventions such as deep cleaning procedures carried out by a veterinarian. The cleaning procedures can be carried out by the veterinarian under anesthetic. In some embodiments, results of a subsequent review of periodontal health of the dog are used to modify the customized recommendation. In other non-limiting embodiments, the subsequent review of the periodontal health comprises a test of swabs taken from a mouth of the dog.

Certain non-limiting embodiments include a system for providing a customized recommendation for a treatment regimen for maintaining oral health of a dog. The system can comprise a processor and a memory that stores computer code that, when executed by the processor, causes the computer system to receive at least one of a first input or a second input. The first and second inputs are characteristics of the dog selected from at least one of (a) a breed of the dog, (b) a shape of the dog's head, (c) a size category of the dog, (d) a weight or body condition of the dog, (e) a predicted size category or weight of the dog as an adult, or (f) a age of the dog. The computer system can also be caused to analyze and transform at least one of the first input or the second input to derive an overall susceptibility level of the dog to periodontal disease via an algorithm. The algorithm can comprise computer code developed from at least one training dataset comprising an occurrence of the periodontal disease in a set of other dogs having the characteristics. In addition, the computer system can be caused to generate an output comprising a customized recommendation for an oral health regimen based on the overall susceptibility level of the dog, and/or display the customized recommendation on a graphical user interface of the system.

In certain non-limiting embodiments, the computer system is caused to compare the weight or the body condition of the dog to an expected weight for the breed or an expected body condition of the dog. The customized recommendation can account for whether the dog is over or under weight or has a poor body condition. Alternatively, or in addition to, the computer system is caused to receive a third input comprising a dental review carried out on the dog. At least one of the first input, the second input, or the third input can be analyzed and transformed to derive the overall susceptibility of the dog to the periodontal disease via the algorithm. The dental review can comprise an analysis of a mouth swab from the dog.

Throughout the description and claims of this specification, the words "comprise" and "contain" and variations of the words, for example "comprising" and "comprises", mean "including but not limited to", and do not exclude other components, integers or steps. Moreover the singular encompasses the plural unless the context otherwise requires: in particular, where the indefinite article is used, the specification is to be understood as contemplating plurality as well as singularity, unless the context requires otherwise.

Preferred features of each aspect of the invention may be as described in connection with any of the other aspects. Within the scope of this application it is expressly intended that the various aspects, embodiments, examples and alternatives set out in the preceding paragraphs, in the claims and/or in the following description and drawings, and in particular the individual features thereof, may be taken independently or in any combination. That is, all embodiments and/or features of any embodiment can be combined in any way and/or combination, unless such features are incompatible.

BRIEF DESCRIPTION OF THE DRAWINGS

One or more embodiments of the invention will now be described, by way of example only, with reference to the accompanying drawings, in which:

FIG. 1A shows 'normal' healthy teeth and gingiva, where although plaque may be present, there are smooth healthy gingiva, no inflammation and no calculus; FIG. 1B illustrates Stage 1 periodontal disease (gingivitis) where there is inflammation, and although plaque and calculus may be present, there is no attachment loss; FIG. 1C shows Stage 2 periodontal disease wherein there is inflammation, swollen gingiva, up to 25% early bone loss and early attachment loss; FIG. 1D shows Stage 3 periodontal disease with inflammation, infection, gingival loss and 25-50% bone loss, and FIG. 1E shows Stage 4 periodontal disease, including infection, gingival recession, exposed tooth roots and over 50% bone loss.

DETAILED DESCRIPTION OF THE INVENTION

Figure 1A:
FIGS. 1A-1E show examples illustrating the stages of periodontal disease used in the studies where
Figure 1B:
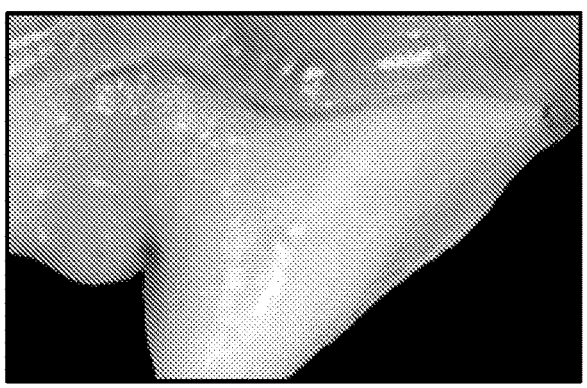
Figure 1C:
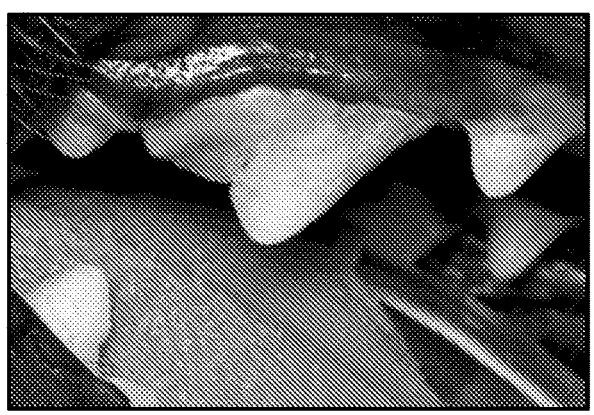
Figure 1D:
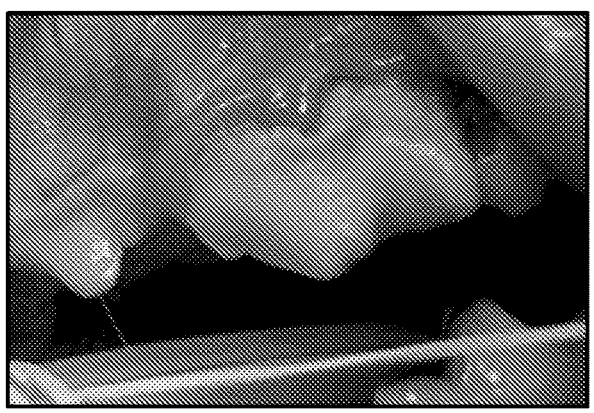
Figure 1E:
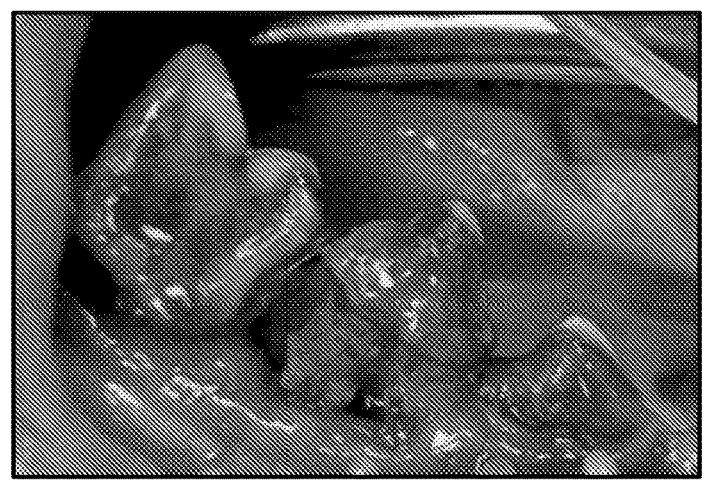

The invention will now be particularly described by way of example only.

Example 1

Analysis of Lifetime Prevalence and Period Prevalence of Periodontal Disease in Pedigree and Mixed-Breed Dogs Lifetime prevalence was defined as the proportion of the dog population diagnosed with periodontitis, or dental calculus, by a particular age with the assumption that dogs had not been previously diagnosed in another veterinary practice. Canine in-patient visits from April 1994 to September 2015 for pedigree dogs of 100 breeds that most frequently visited a number of US vets and dogs identified as "mixed breed" were included in the lifetime prevalence analysis. Dogs described as non-pedigree were excluded as it was not clear if they were actually "mixed breed" or non-papered pedigrees.

Data was extracted from electronic medical record database for veterinary visits where periodontal disease was diagnosed (ailment descriptions included periodontal disease, periodontal pocket and periodontal disease grades 1, 2, 3 and grade 4). Information about the pet identification number (pet ID), breed, age at the date of the visit, first and last ages in the database, death age (if applicable), and the diagnosis were extracted. Only dogs aged between 2 and 16 years over the study period were included.

Breeds were categorised according to average adult weight (2.5 and 10 years old) of the individuals, where there was no adverse body condition score or weight control comments recorded in the veterinary notes.

The mixed breed category was manually split into 5 kg weight categories, and each group assigned to the relevant breed size category. Size categories were defined by weight cut-off values established from puppy growth data.

The age at first diagnosis for periodontal disease and dental calculus was determined. Periodontal disease encompasses gingivitis and periodontitis, and, therefore, only the terms "periodontal pocket" and "periodontal disease grades 3 and 4" were used as definition of periodontitis. In addition, a number of dogs were classified as having the ungraded ailment "periodontal disease" which was assumed to be equivalent to periodontal disease grades 1 to 4. The split between grades 1-2 and 3-4 was therefore estimated by determining the proportion of dogs that had progressed from grades 1-2 to grades 3-4 over the study period with the assumption that all dogs started at grades 1-2. This proportion was then added to the "periodontal pocket" and "periodontal disease grades 3 and 4" data to give a total periodontitis prevalence at ages 2 through to 16 years. Dental calculus ailment descriptions included "dental calculus" and "dental calculus subgingival".

In a second study, period prevalence, defined as the proportion of dogs that developed periodontal disease or dental calculus over a five-year period, was evaluated. It included dogs that already had the periodontal disease or dental calculus at the start of the study period or developed the conditions during the period.

Selection of Top 10 Breeds for Each Size Category

The ten most common breeds of dog were identified from six size categories which were again defined by weight cut-off values established from puppy growth data (WALTHAM® puppy growth chart). Using data that had previously been extracted for canine in-patient visits from 1 Jan. 2004 through 8 Aug. 2014, the median weights (at visit) of adult dogs (at least 2 years of age) that were not indicated to be of mixed breed were used to assign the breed to a size category (Table 8). The top ten breeds of dogs in each size category were identified, based on the number of unique dogs of those breeds that visited a number of US vets over a 5-year period, 2010 through 2014. These top ten breeds represented 95.3% of the extra-small breed size category, 96.8% of the small, 92.7% of the medium-small, 84.5% of the medium-large, 97.1% of the large and 73.3% of the giant category.

Data Selection

Canine in-patient visits from 1 Jan. 2010 through 31 Dec. 2014 for the 60 breeds detailed in Table 8 were extracted from the veterinary electronic medical record database. Variables extracted for each visit included: pet ID, breed, age (in months), gender, neuter status, weight, body condition score (BCS), enrolled on Optimal Wellness Plans® (OWP), time on OWP (in months), dental prophylaxis performed at visit, time since last dental prophylaxis (if known, in months), total number of dental prophylaxis during the study period, diagnosis of periodontal disease (ailment descriptions included periodontal disease, periodontal pocket, gingival recession, periodontal disease grade 1, grade 2, grade 3 and grade 4) and dental calculus (ailment descriptions included dental calculus, dental calculus subgingival and dental tartar). OWP are a pre-paid package of services onto which pet owners can enroll their pet. The services included vary depending on the pet age and on the options that owners choose. Annual dental cleaning is one of the services that may be included. See FIG. 1 for definitions of the stages of periodontal disease used as guidelines for veterinarians to diagnose and stage periodontal disease.

Dogs were excluded from the study if any of the following information occurred in the pet record: no birth date, negative age recorded on any visit, the recorded birth date is after the recorded death date, the gender is unknown, or duplicate records exist for that pet. For the study, the visit for a dog was included in the analysis when the pet's age at visit is at least 6 months but no greater than 25 years. If a pet was diagnosed with periodontal pocket and/or gingival recession along with a graded periodontal disease diagnosis then the pet was considered to have the graded diagnosis. Likewise, if a pet received a diagnosis of gingivitis (grade 1) and a higher grade on the same visit then the pet was deemed to have the higher grade. If a pet's record indicated more than one in-patient visit on a day, the information from those visits were consolidated into one visit for that day.

The median weight of each dog over the study period was determined, and then the median weight for each breed calculated. For each visit, the difference in body weight from the breed median weight was then determined. Pet visits where the pet weight was not within two standard deviations of the median weight for the breed had the pet weight set to 'missing' for that visit. BCS was either recorded on a 5-point scale (1=malnourished, 3=normal, 5=obese) or entered as a diagnosis of overweight/obese or underweight/emaciation. It was not a pre-requisite for the BCS (5-point scale) to be entered in a pet's visit record until July 2014, and this was only required on the first visit and then was carried over into subsequent visits unless consciously changed by a hospital team member on a subsequent visit. Prior to July 2014, if no BCS or diagnosis to indicate non-normal body condition or diagnosis was recorded, it was assumed to be normal because the default BCS seen at the hospital (but not recorded in the pet record unless purposely selected by a hospital team member) was normal. In cases where multiple entries for the pet on the same day occurred or there were conflicting entries, the non-normal body condition score was used (e.g., a pet's visit had both BCS entry of "normal" and diagnosis of overweight—this pet was considered overweight on that visit). For statistical analysis all BCS were converted onto a three-point scale (1=underweight, 2=ideal, 3=overweight).

Statistical Analysis

Study 1—Lifetime Prevalence

Kaplan-Meier survival curves were calculated for each periodontitis and calculus definition, to show the cumulative risk of having had at least one diagnosis of the relevant condition by age. The calculation was based on the number of individuals at risk and the number diagnosed with periodontitis or calculus at each time point. As Kaplan-Meier curves are step curves (each step occurs when an event happens to an individual, in this case a diagnosis of periodontitis or calculus) the curves were smoothed using loess smoothing (smoothing span was set at 0.25). The prevalence curve was then calculated as one minus the smoothed Kaplan-Meier survival curve. This was calculated at one year intervals from age 2 to 16 to account for the fact that ages are frequently rounded to the nearest year by owners and/or veterinary staff.

The association of periodontitis and calculus prevalence curves (log transformed) with breed size category was determined using functional ANOVA. P-values were adjusted for multiplicity using Bonferroni correction. Statistical analysis was carried out in R 2.15.2, using packages fda and fda.usc.

Study 2—Period Prevalence

Multivariate mixed effect models were built using PROC NLMIXED in SAS 9.4 (SAS Institute, Cary, NC, USA), to allow for repeat observations for individuals, with pet ID as the mixed effect variable, with models for each breed size category, using backward stepwise selection. Models were built for each outcome (periodontal disease and dental calculus) as binary outcomes (yes/no). To establish the reference breed in each size category, the breed with the largest population in the category was used. The most frequently seen breed within each breed size category were Chihuahua (extra-small), dachshund (small), beagle (medium-small), pit bull (medium-large), Labrador retriever (large) and Rottweiler (giant). Due to the large number of visits for the dogs included in this study, using PROC SURVEYSELECT, a 1-in-20 random sampling of dogs in the extra-small through large size category and a 1-in-5 random sampling of giant dogs was made, and all pet visits for those selected dogs during the study period were used for developing the regression models. Subsequently, using PROC MULTTEST pair-wise comparisons with Bonferroni correction were undertaken to identify breed size category and breed differences in risk for periodontal disease and dental calculus, controlling for the variables in the respective models. Results were considered to be significant if p<0.0036 due to Bonferroni correction for multiplicity.

Results

Study 1—Lifetime Prevalence of Periodontitis and Dental Calculus

The dataset used to determine the lifetime prevalence for periodontitis and dental calculus comprised 20 extra-small, 12 small, 17 medium-small, 26 medium-large, 14 large and 11 giant breeds of dog. Dogs described as mixed breed were also included in each of the six breed size categories based on their weight. A total of 414,366 dogs were included in the analysis.

Figure 2:
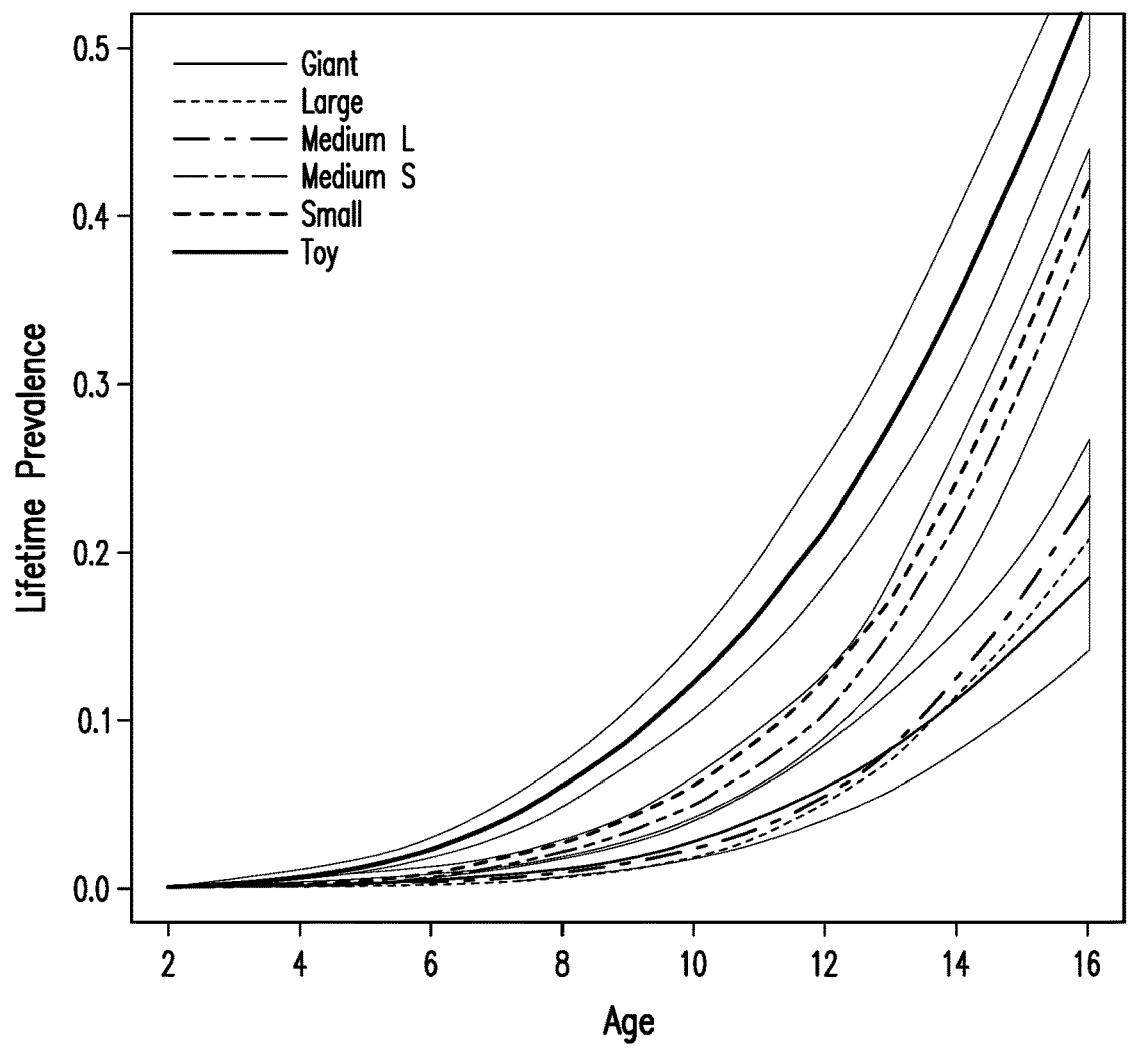
FIG. 2 shows mean lifetime prevalence curves for periodontitis for each breed size category with 95% confidence intervals. The six different shaded lines represent each of the breed size categories (see legend) and the shading depicts 95% confidence intervals.

There was a significant difference between the mean lifetime prevalence curves for periodontitis for the different breed size categories (p<0.0001; FIG. 2). Pairwise comparisons of breed size categories showed that they were all significantly different from each other (all p<0.0001). The lifetime prevalence of periodontitis was highest for the extra-small breed size category compared to the other larger breed size categories. The small and medium-small categories had the next highest lifetime prevalence with the medium-large, large and giant breed size categories having the lowest.

Figure 3:
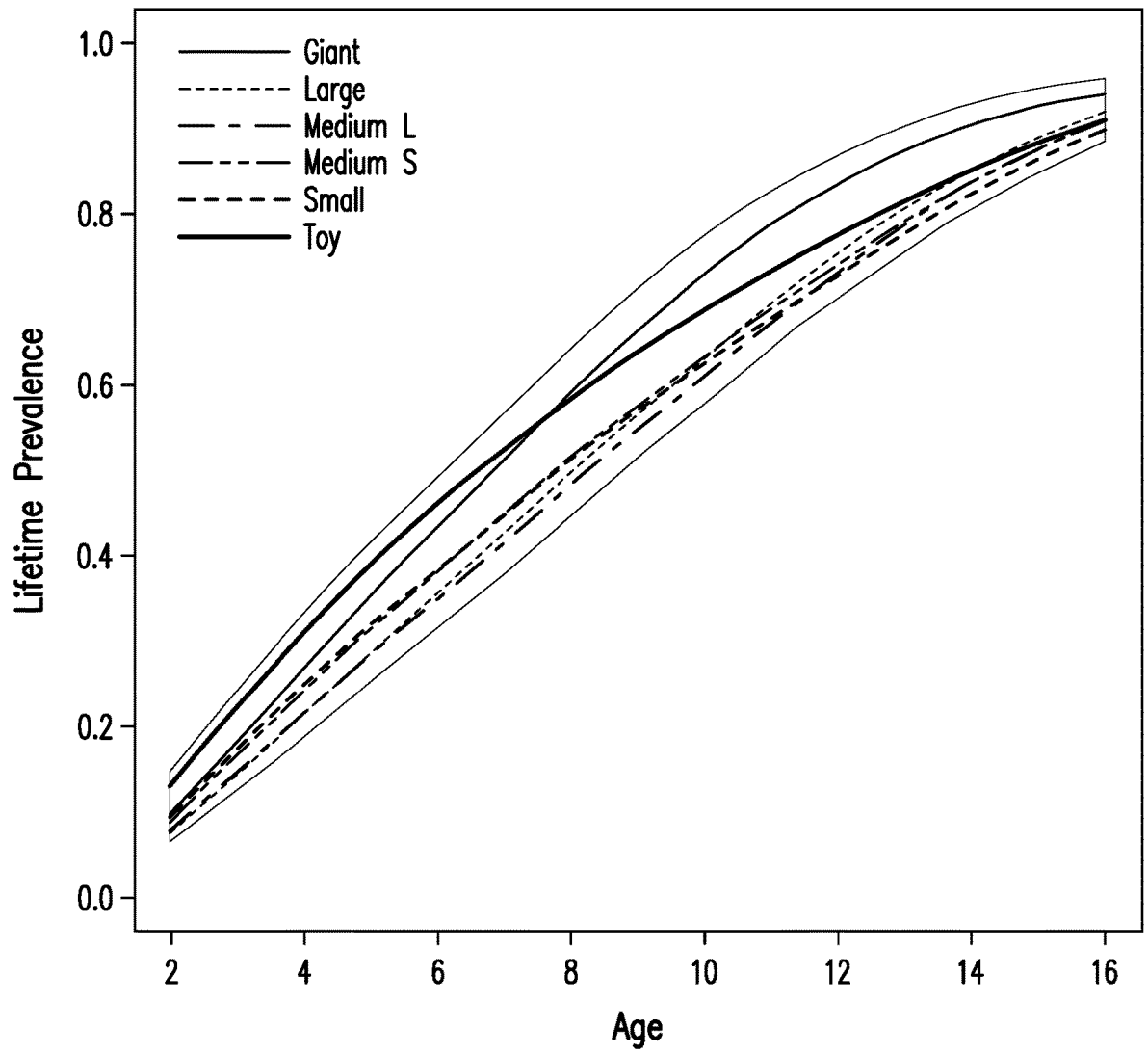
FIG. 3 shows mean lifetime prevalence curves for calculus for each breed size category with 95% confidence intervals. The six different lines represent each of the breed size categories (see legend) and the shading depicts 95% confidence intervals.

The mean lifetime prevalence curves for dental calculus for the six breed size categories are shown in FIG. 3. Up to approximately six years of age extra-small breeds had a significantly higher lifetime prevalence of dental calculus than the other breed size categories, with the exception of giant, (p<0.05). At approximately eight years of age the giant breed size category begins to have a higher lifetime prevalence of dental calculus than the extra-small breeds and this difference is significant by thirteen years of age (p<0.05). Although giant breeds are not long-lived, these data sets were still reasonably sized; 8 of the 13 giant breeds analysed had at least 400 individuals not yet having developed calculus at 10 years of age and all but one of these had at least 100 individuals still to develop calculus at 12 years of age.

Study 2—Period prevalence of Periodontal Disease and Dental Calculus Study Population Over the five year study period, a total of 5,787,581 dogs were seen in 31,306,476 visits to a number of US vets. Of these 3,320,519 dogs (57.4%) or 18,233,668 visits (58.4%) were the 60 breeds selected for this study. After application of the exclusion criteria 2,841,038 dogs (85.6%) with 14,746,691 visits (80.9%) were included in the study population (Table 9). Extra-small dogs were the most common breed size group to visit vets during the study period, representing 36.9% of dogs compared to less than 20% for each of the other breed size categories.

The average age at the time of visit was 61.8 months (5.1 years; +/−44.1 months). There were slightly more male dogs (52.7%) than female dogs (47.3%), and the majority (70.8%) had been spayed/neutered (Table 10). The average weight at visit of the extra-small breeds was 4.7 kg (+/−2.0 kg), small breeds was 7.6 kg (+/−2.3 kg), medium-small breeds was 12.1 kg (+/−3.8 kg), medium-large breeds was 25.9 kg (+/−6.5 kg), large breeds was 34.2 kg (+/−7.7 kg) and giant breeds was 45.7 kg (+/−11.5 kg; Table 3). The majority of dogs (74.2%) had a normal BCS at the time of their visit (Table 3). However, there were 6,638,197 visits (45.0%) where it was necessary to assume that the body condition score was ideal for these visits (see methods section for explanation). There were a small percentage of visits where the dogs were recorded as underweight (1.8%) and a greater number that were recorded as overweight (23.9%). Table 11 shows the age, sex, weight and BCS at visit for each of the 60 breeds.

Over half of the dogs (56.9%) had been enrolled on an OWP during the study period, with approximately 81.2% of the in-patient visits occurring while the dogs were enrolled on an OWP. This was similar for all the breed size categories (Table 12).

On average, the dogs had less than one prophylactic dental cleaning under general anaesthesia during their time on the study, and this decreased as the breed size increased (Table 13). On average 31.8% of the dogs underwent a dental cleaning in the year prior to the visit, while for 62.2%, there was no known history of dental cleaning prior to the visit. Less than 8% of the visits were found to occur greater than 12 months after a recorded dental cleaning. There was a decrease in the number of dental cleanings a pet had undergone during the study period as the breed size increased (Table 13). A dental cleaning was performed in 8.6% of the in-patient visits during the study period. The extra-small and small breed size categories had the greatest number of dental cleanings performed during the visit: Average across all breeds for extra-small and small size categories was 9.7% and 10.7%, respectively, and the giant breed size category had the fewest (6.1%). Table 14 shows the dental cleaning summaries for each of the 60 breeds included in this study.

Period Prevalence of Periodontal Disease

The overall period prevalence of periodontal disease was 18.2% (517,113 cases). The majority of dogs were diagnosed with periodontal disease stage 1 (10.3%) which is gingivitis. A further 5.7% were diagnosed as grade 2 (<25% attachment loss), 3.5% as grade 3 (25% to 50% attachment loss) and 1.9% as grade 4 (>50% attachment loss).

The prevalence was highest in the extra-small, small and medium-small size categories compared to medium-large, large and giant (Table 15). The twenty breeds with the highest prevalence of periodontal disease (grades 1-4) were: greyhound (38.7%), Shetland sheepdog (30.6%), papillon (29.7%), toy poodle (28.9%), miniature poodle (28.2%), dachshund (28.1%), bichon frise (27.9%), Cavalier King Charles spaniel (27.3%), American Eskimo (27.0%), Cairn terrier (26.8%), West Highland white terrier (26.6%), Pomeranian (26.4%), rat terrier (26.0%), fox terrier (25.6%), Yorkshire terrier and Maltese (each 25.4%), basset hound (25.3%), American cocker spaniel (25.3%), miniature schnauzer (23.7%) and beagle (23.2%; Table 165). All but two breeds, greyhound and basset hound, were in the medium-small, small or extra-small size categories. All of the giant breed dogs, with the exception of the Bernese mountain dog, were among the lowest 20 breed prevalence estimates, with the cane corso the lowest (4.0%).

The random selection of pets for the regression models led to the creation of a subpopulation of 152,621 pets (5.4% of study population), which accounted for 777,390 (5.3%) in-patient visits, for the regression analysis. The breed size and breed regression models found that being of non-normal body condition significantly increased the odds of periodontal disease diagnosis. All models showed that being overweight significantly increased the risk of periodontal disease (odds ratio (OR)=1.65 to 2.90, all p<0.001) whereas only the breed size, extra-small and giant breed models identified being underweight as increasing the odds (OR1.15 to 1.77, p=0.002 for breed size and p<0.0001 for extra-small and giant models). Overall, only the breed size and extra-small breed models showed a significant effect of weight on the probability of periodontal disease. Dogs with a body weight greater than the median weight for their breed had a slightly increased odds of periodontal disease diagnosis in the breed size model, but slightly decreased odds in the extra-small breeds (OR=1.01 and 0.98 respectively, both p<0.0001). All models showed that the odds of periodontal disease significantly increased with age, although the increases were small (OR=1.03 to 1.05, all p<0.0001). Only the extra-small and giant breed models showed a significant effect of neuter status on the prevalence of periodontal disease, although the findings were contradictory. Extra-small breeds had a decreased odds of periodontal disease if spayed/neutered (OR=0.98, p<0.0001) but giant breeds had an increased odds (OR=1.23, p<0.0001).

All breed size models showed that if there was no record of a dental cleaning having occurred prior to the visit, the odds of periodontal disease diagnosis were increased (OR 1.95 to 6.01, all p<0.0001). Likewise, in all except the small breed model, the number of dental cleanings significantly increased the probability of periodontal disease diagnosis. The OR increased from 1.26 for extra-small breeds up to 1.40 for giant breeds (all p<0.0001). Likewise if a dental cleaning was performed at the time of the visit the odds of periodontal disease diagnosis was significantly increased across all models (OR=1.46 to 2.91, all p<0.0001). The time since last dental cleaning was associated with an increased odds of periodontal disease diagnosis. Relative to a visit that occurred within 12 months of a dental cleaning, the odds of periodontal disease diagnosis increased for all models (OR=1.41 to 4.52, p=0.0007 for medium-large breed model and all others p<0.0001). If it was two or more years since last dental cleaning the odds of periodontal disease diagnosis increased (OR=1.68 to 5.26, p=0.0013 for medium-large breed model and p<0.0001 for all others). All models, except extra-small and medium-small breeds, showed that time on an OWP during the study period only slightly increased the odds of periodontal disease diagnosis (OR=1.03 to 1.02, all p<0.0001). The breed size model suggested that if a dog was on an OWP at the time of visit it was more likely to be diagnosed with periodontal disease during the visit (OR=1.14, p<0.0001).

Figure 4:
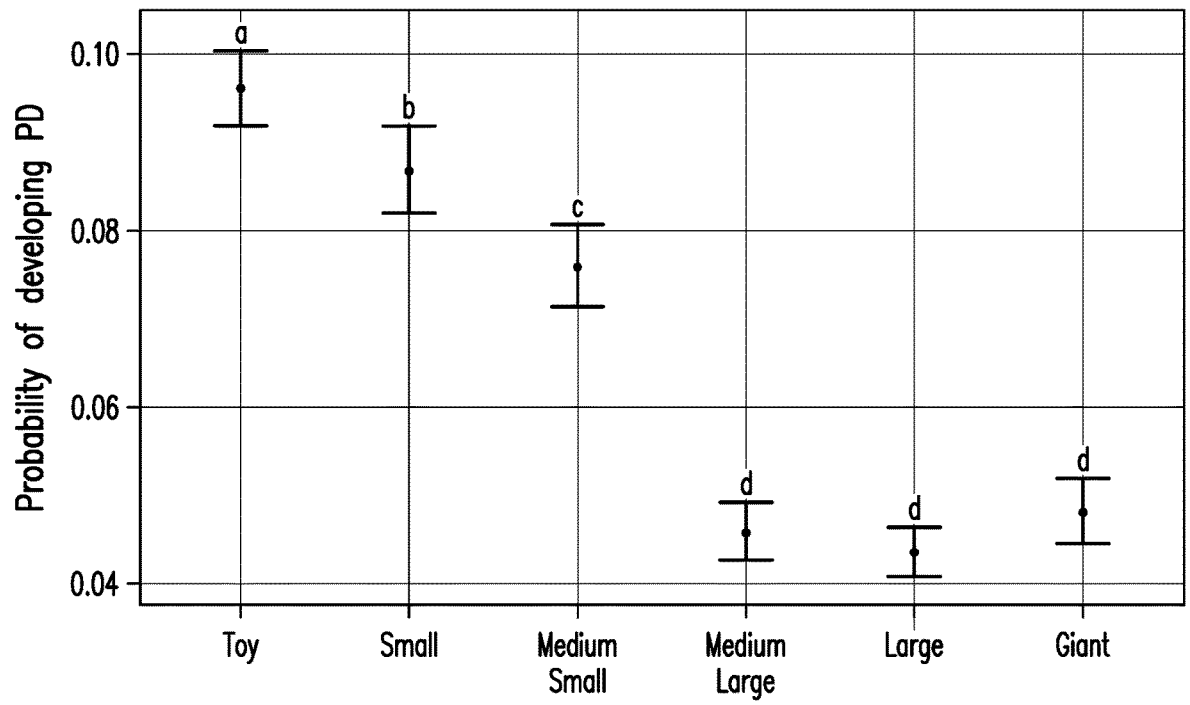
FIG. 4 is a graph showing the probability of developing periodontal disease at 60 months of age for each breed size category. Bars indicate 95% confidence intervals and letters depict Bonferroni groups (If different this denotes that size categories are significantly different at p=0.0036).

Pairwise comparison of the breed size categories for periodontal disease showed that the extra-small breed size group had a significantly higher probability of periodontal disease compared to all the other breed size categories (all p<0.0001; FIG. 4). The small breed size category had the next highest probability and was significantly different to all other breed size categories (all p<0.0001). The medium-small size category had a significantly higher probability of periodontal disease diagnosis than medium-large, large and giant breed size categories (all p<0.0001). The medium-large, large and giant breed size categories were not significantly different from each other (p>0.0036). The OR increased as breed size increased ranging from 1.25 (comparing extra-small to small breeds) up to 4.38 (comparing extra-small to giant breeds).

Figure 5A:
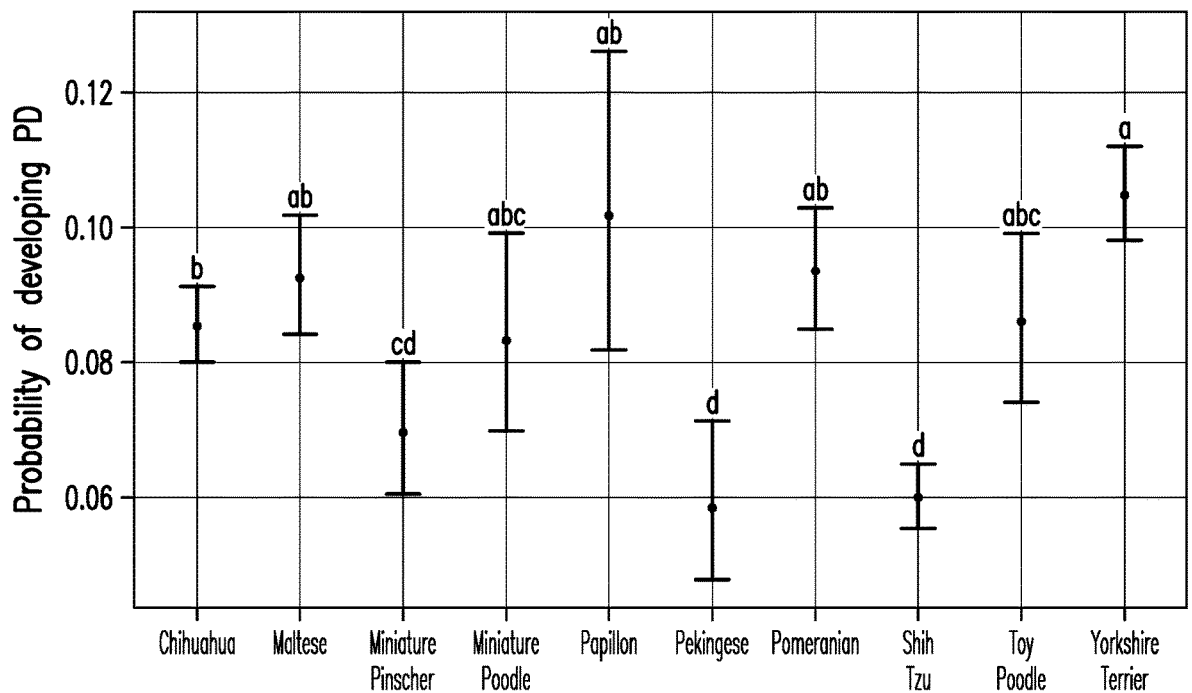
FIGS. 5A-F are a series of graphs showing the probability of developing periodontal disease at 60 months of age for top ten breeds in each breed size category FIG. 5A—extra-small, FIG. 5B—small, FIG. 5C—medium-small, FIG. 5D—medium-large, FIG. 5E—large and FIG. 5F—giant. Bars indicate 95% confidence intervals and letters depict Bonferroni groups (If different this denotes that breeds are significantly different at p=0.0036).

The individual breed size models found significant breed differences in the probability of periodontal disease. Pairwise comparisons of the extra-small breeds showed that Yorkshire terriers had the highest probability of periodontal disease but they were not statistically different to Maltese (p=0.02), miniature poodle (p=0.008), Papillon (p=1.0), Pomeranian (p=0.07) and toy poodle (p=0.005) (FIG. 5A). Pekingese and Shih Tzu had the lowest probability of periodontal disease compared to all other extra-small breeds (p=0.0032 to p<0.0001) but were not significantly different from each other (p=1.0) or miniature pinscher (p=0.16). The odds of a Yorkshire terrier having periodontal disease was 3.15 that of a Pekingese (p<0.0001).

Figure 5B:
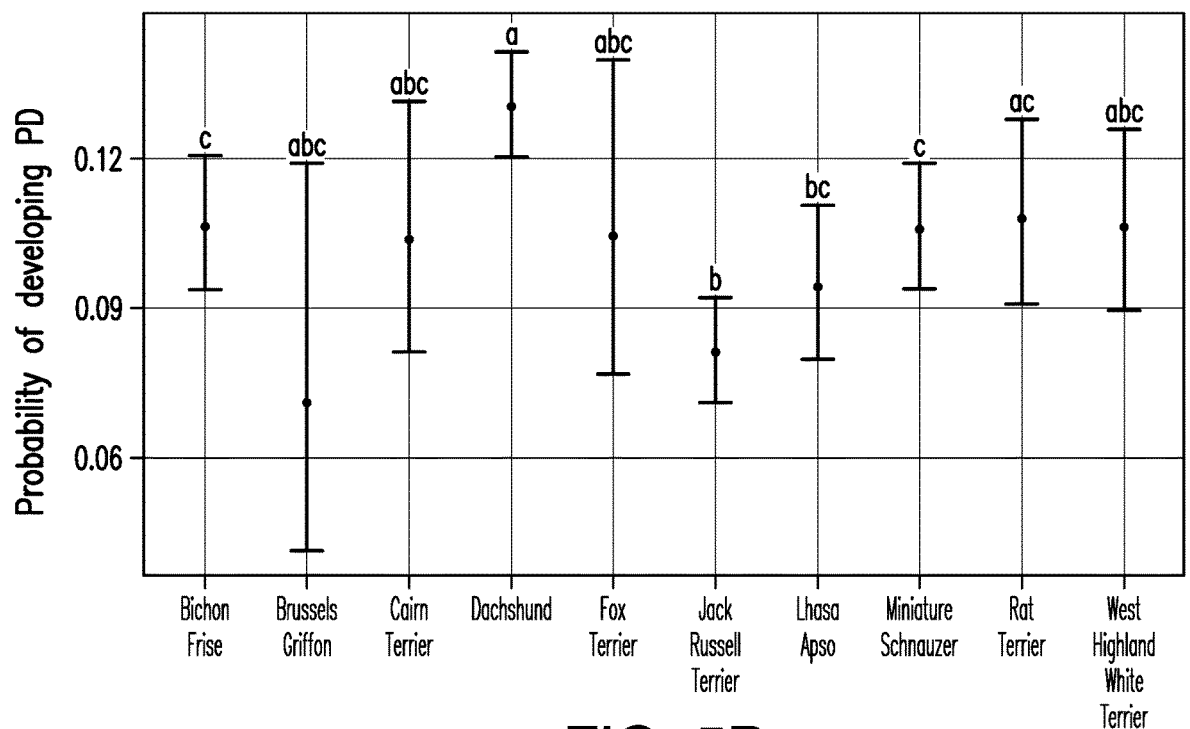

Within the small breed size category dachshund had the highest probability of periodontal disease, although they were only significantly different than bichon frise (p=0.0007), Jack Russell terrier (p<0.0001), Lhasa Apso (p<0.0001) and miniature schnauzer (p=0.0001; FIG. 5B). Jack Russell terriers had a significantly lower probability of periodontal disease than bichon frise (p<0.0001), dachshunds (p<0.0001), miniature schnauzers (p<0.0001) and rat terriers (p=0.002). The odds of a dachshund being diagnosed with periodontal disease was 2.56 that of a Jack Russell terrier.

Figure 5C:
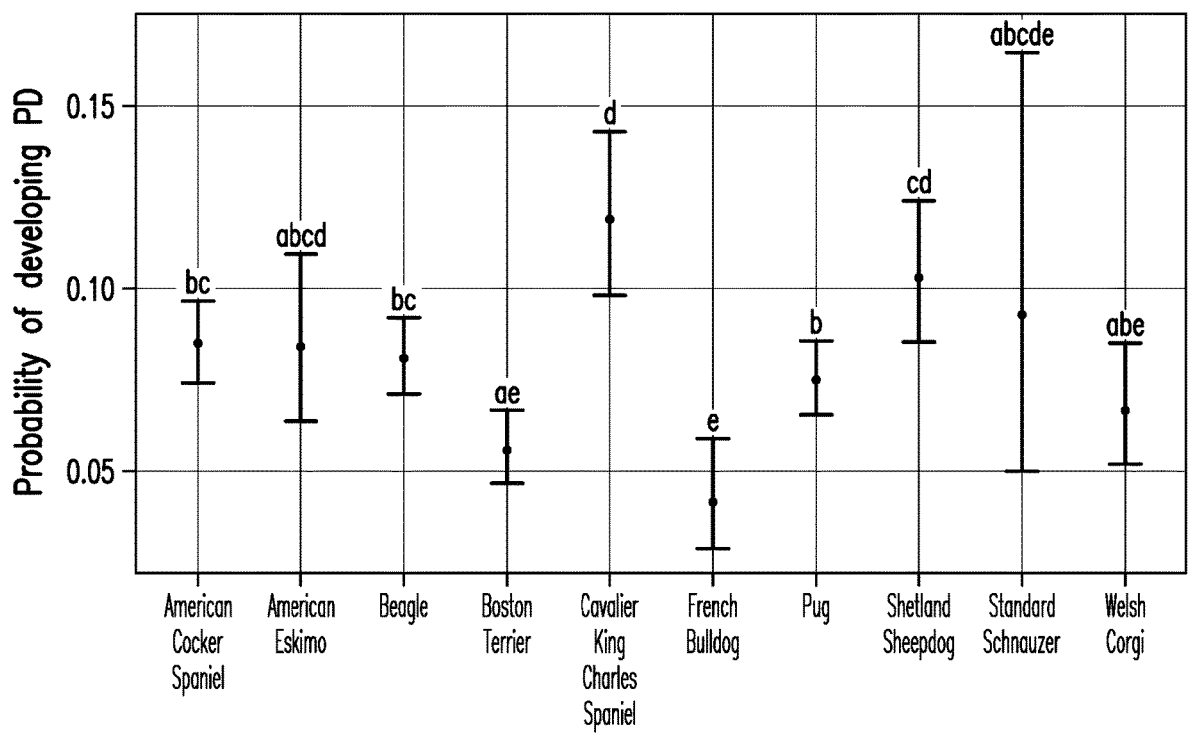

Cavalier King Charles spaniel had the highest probability of periodontal disease within the medium-small size category but was not significantly different than American Eskimo (p=0.053), Shetland sheep dog (p=1.0), and standard schnauzer (p=1.0; FIG. 5C). The French bulldog had the lowest probability of periodontal disease but was not significantly different than the Boston terrier (p=0.95), standard schnauzer (p=0.037) and Welsh corgi (p=0.034). The odds of a Cavalier King Charles spaniel having periodontal disease was 8.09 that of a French bulldog (p<0.0001).

Figure 5D:
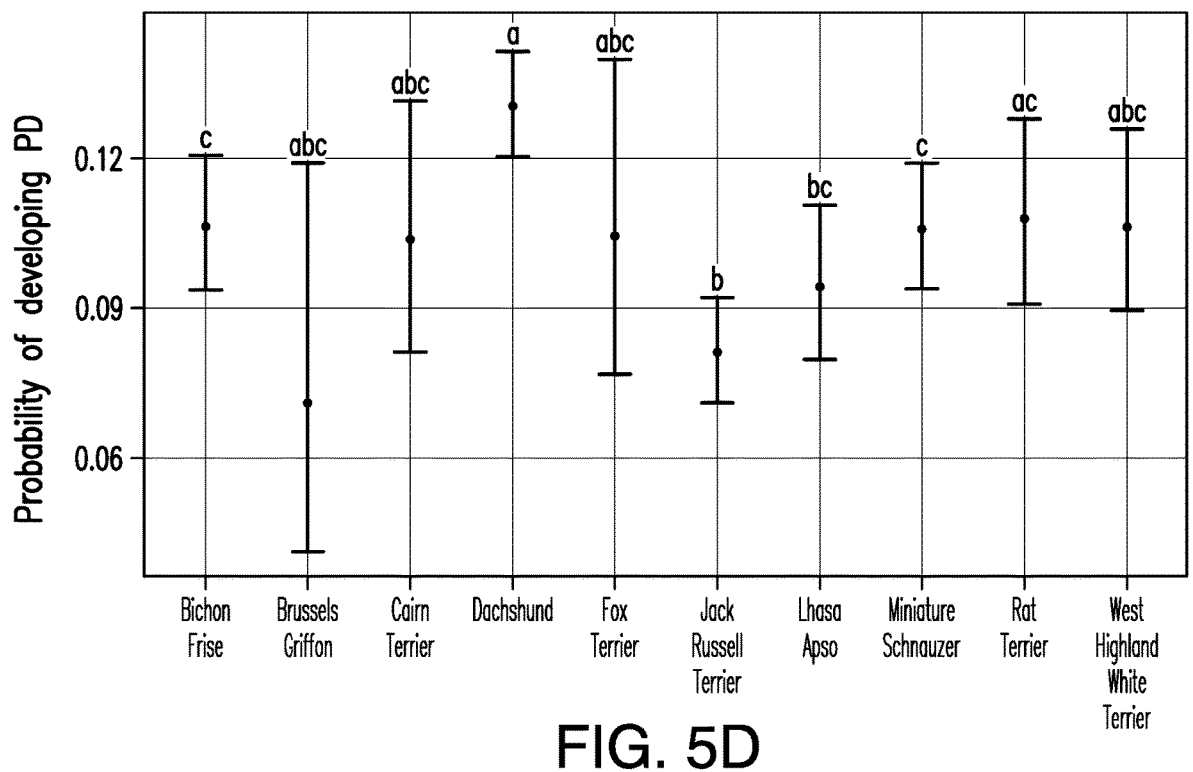

In the medium-large breed size group, basset hounds had the highest probability of periodontal disease, and this was significant compared to all other breeds (all p<0.0001) with the exception of the standard poodle (p=0.322; FIG. 5D). The English bulldog had the lowest probability of periodontal disease but this was only significantly lower than Australian shepherd, basset hound, and standard poodle (all p<0.0001). The odds of a basset hound having periodontal disease was 10.08 that of an English bulldog.

Figure 5E:
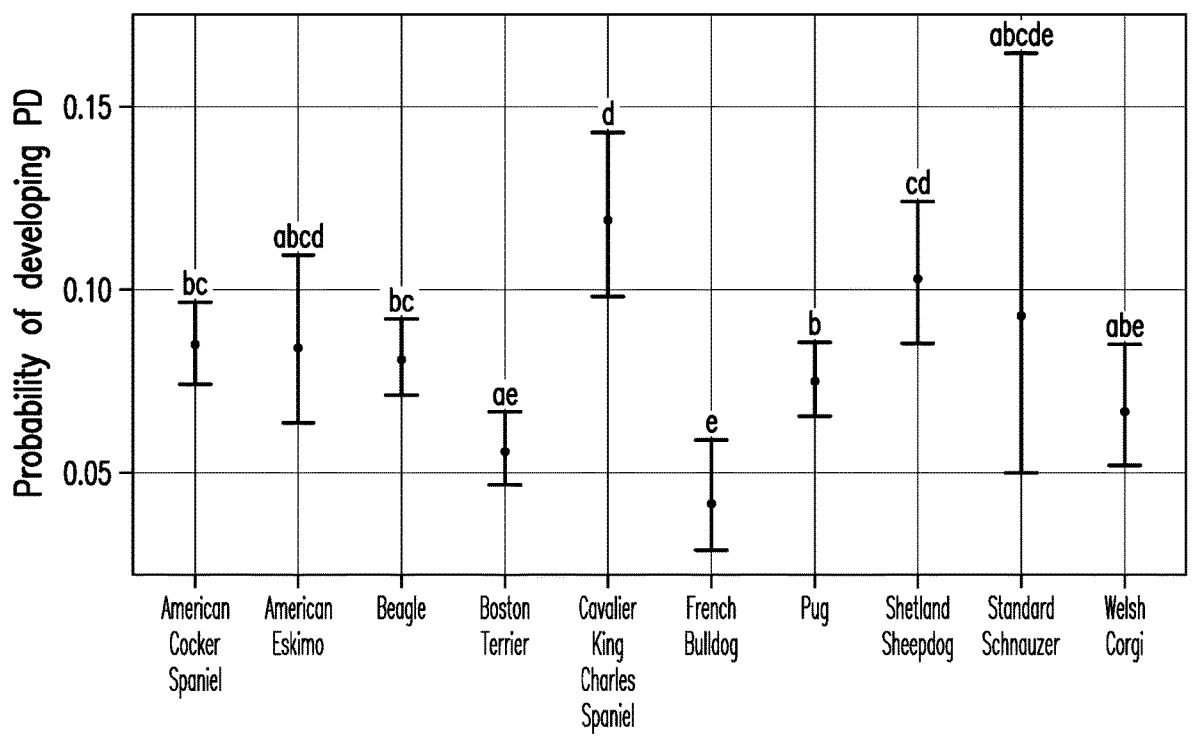

Investigation of inter-breed differences in the large breed size category showed that greyhounds had a significantly higher probability of periodontal disease compared to the other nine large breeds (all pairwise comparisons p<0.0001; FIG. 5E). The odds of a greyhound having periodontal disease compared to the other breeds ranged from 14.3 to 35.5. There was no significant difference in the probability of periodontal disease between the other breeds (all p>0.0036).

Figure 5F:
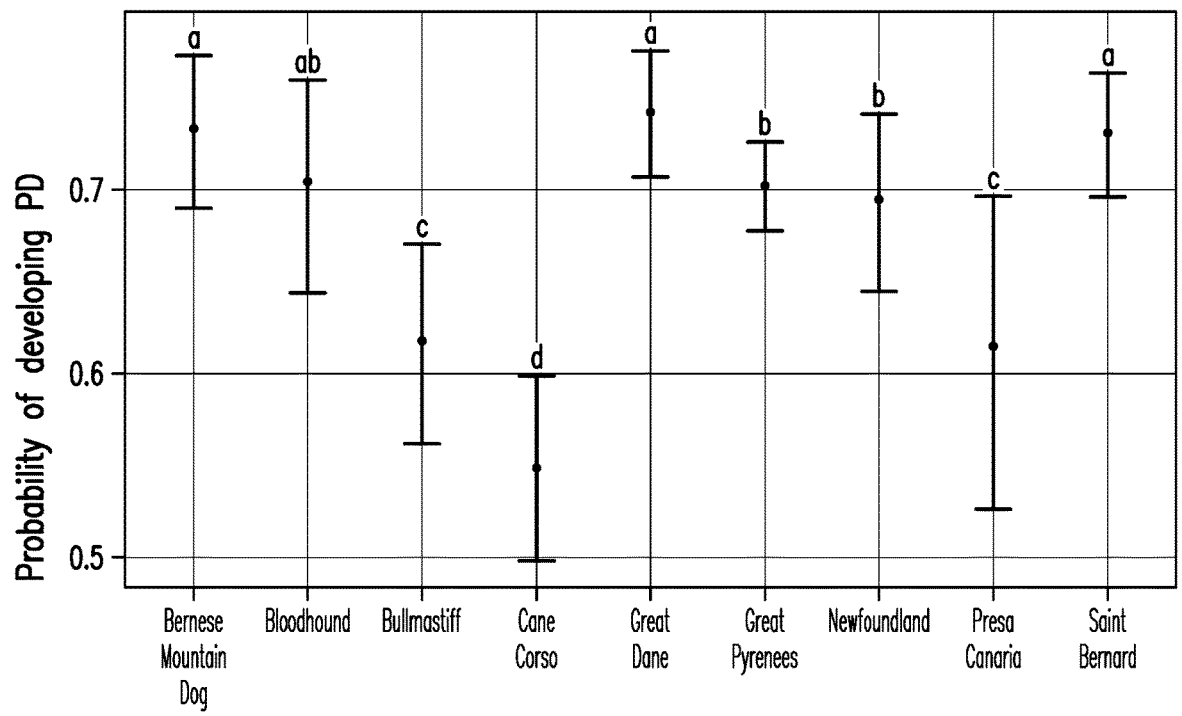

In the giant breed size category Bernese mountain dogs, great Danes and Saint Bernard had a significantly higher probability of periodontal disease than all other breeds (p=0.007 to <0.0001) with the exception of the blood hound (p=0.004 and 0.37; FIG. 5F). Cane corso had a significantly lower probability of periodontal disease than all other breeds (p=0.0009 to <0.0001). The odds of a great Dane having periodontal disease was 4.32 that of a cane corsa (p<0.0001).

Period Prevalence of Dental Calculus

The five-year prevalence of dental calculus across all breeds was 74.5%. The prevalence of dental calculus was greatest among the extra-small (78.3%), small (83.5%) and medium-small (80.6%) breeds compared to medium-large (60.3%), large (71.0%) and giant (63.7%) breed size categories (Table 15). The twenty breeds of dog with the highest prevalence of dental calculus included many of breeds that had the highest prevalence of periodontal disease: greyhound (89.2%), Shetland sheepdog (87.3%), Cairn terrier (86.4%), West Highland white terrier (85.9%), papillon (85.4%), Lhasa apso (85.0%), American cocker spaniel (84.7%), bichon frise (84.5%), rat terrier (84.4%), fox terrier (84.0%), American Eskimo (83.8%), dachshund (83.2%), miniature poodle (83.1%), basset hound (83.1%), Pekingese (83.0%), beagle (82.7%), Cavalier King Charles spaniel (82.6%), toy poodle (82.5%), Jack Russell terrier (82.2%), and miniature schnauzer (81.9%; supplementary table 5).

Again, similar to periodontal disease prevalence, all of the giant breed dogs with the exception of the Bernese mountain dog, were among the lowest 20 breed prevalence estimates, with the cane corso the lowest (42.9%).

The breed size and breed regression models for dental calculus showed that being overweight or underweight increased the odds of dental calculus (OR=1.78 to 2.72, all p<0.0001). Being female slightly increased the odds of dental calculus diagnosis for all statistical models with the exception of the small breed model (OR=1.12 to 2.10, all p<0.0001). Being neutered increased the odds of dental calculus diagnosis for the breed size and large breed regression models (OR=1.12 to 1.24, all p<0.0001) but decreased the odds for the extra-small breed model (OR=0.84, p<0.0001) and had no effect on the small, medium-small, medium-large and giant models. Age and weight at visit only slightly increased the dental calculus risk (OR=1.02 to 1.11, all p<0.0001). As time since last dental cleaning increased the risk of dental calculus increased: if a dental cleaning was performed 1-2 years prior to visit the ORs ranged 3.87 to 6.2 (all p<0.0001), if more than two years the ORs ranged from 6.83 to 11.91 (all p<0.0001). No history of dental cleaning prior to visit increased the odds of being diagnosed with dental calculus (OR=4.38 to 7.48, all p<0.0001). The number of dental cleanings during the study period increased the risk of dental calculus diagnosis for the medium-large and giant size categories (OR=1.36 and 1.41, all p<0.0001) but had no effect on the breed size categories. If a dental cleaning was performed at the time of the visit the odds of dental calculus diagnosis increased slightly for the breed size category, extra-small, medium-large, large and giant (OR=1.09 to 1.68, all p<0.0001) but there was no significant effect with respect to the small and medium-small breeds. There was a very small increase in the odds of dental calculus diagnosis as length of time on the OWP increased (OR=1.01 and 1.03, all p<0.0001).

Figure 6:
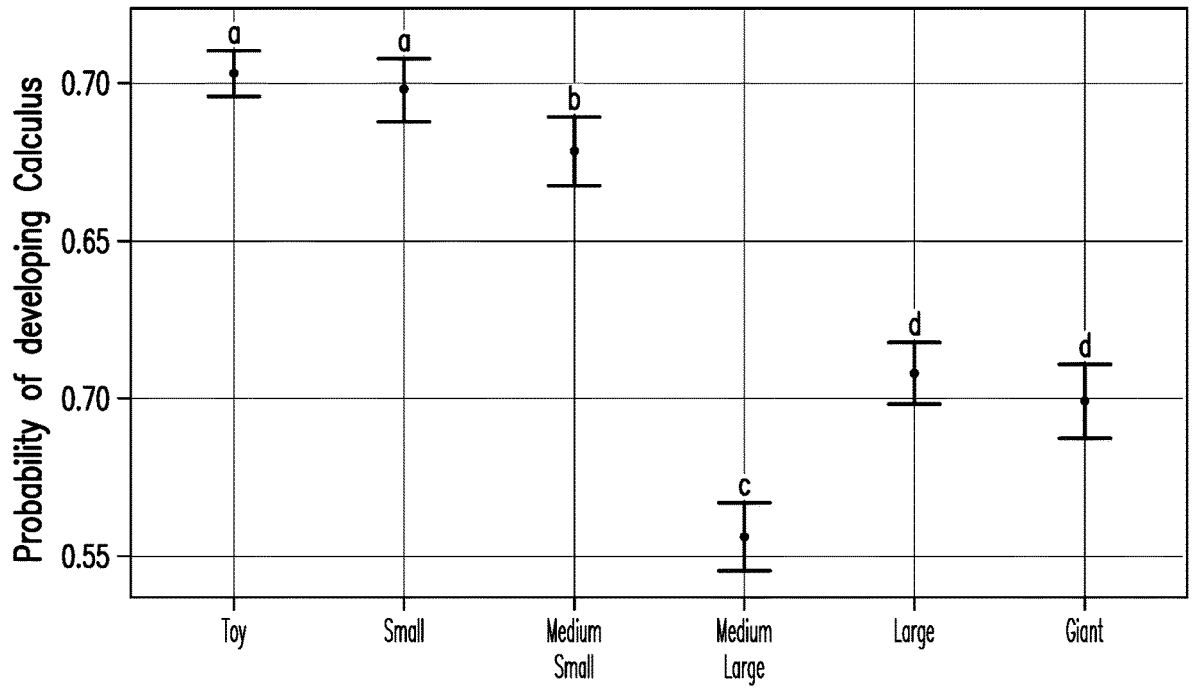
FIG. 6 is a graph showing the probability of developing calculus at 60 months of age for each breed size category. Bars indicate 95% confidence intervals and letters depict Bonferroni groups (If different this denotes that size categories are significantly different at p=0.0036).

Pairwise comparisons of the six breed size categories showed that the probability of dental calculus resembled the patterns seen for periodontal disease in that the extra-small, small and medium-small size categories had a significantly higher probability of calculus than the medium-large, large and giant breeds (FIG. 6). Extra-small and small breed size categories had a significantly higher probability of calculus than all other breed size categories (all pairwise comparisons p<0.0001) but were not significantly different from each other (p=1.0). Medium-small breeds had a significantly higher probability of calculus than medium-large, large and giant (all comparisons p<0.0001). Medium-large breeds had the lowest probability of calculus which was significantly lower than all the other breed size categories (all p<0.0001). The large and giant breed size categories did not differ in their probability of calculus (p=0.42). The odds of the extra-small breed size category having dental calculus was 2.87 that of the medium-large size category.

Figure 7A:
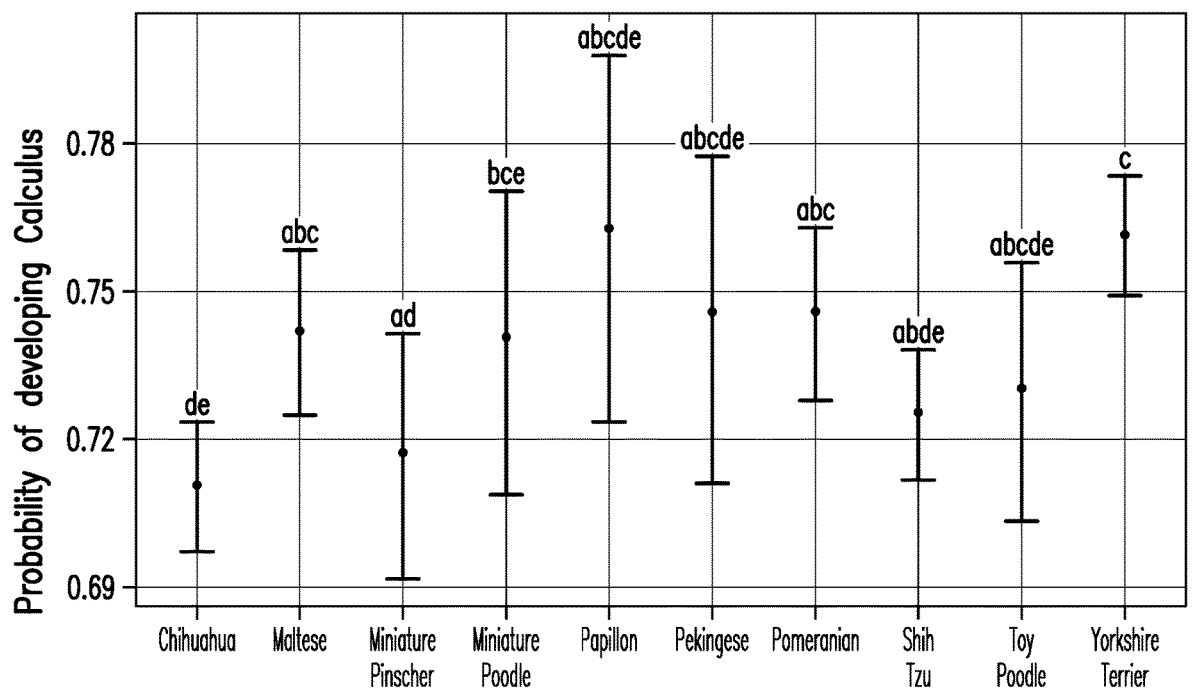
FIGS. 7A-7F are a series of graphs showing the probability of developing calculus at 60 months of age for top ten breeds in each breed size category FIG. 7A—extra-small, FIG. 7B—small, FIG. 7C—medium-small, FIG. 7D—medium-large, FIG. 7E—large and FIG. 7F—giant. Bars indicate 95% confidence intervals and letters depict Bonferroni groups (If different this denotes that breeds are significantly different at p=0.0036).

Looking at inter-breed differences, most of the breed comparisons in the extra-small breeds showed no significant differences in risk for dental calculus (FIG. 7A). However, Yorkshire terriers had a significantly higher probability of dental calculus than Chihuahua (p<0.0001), miniature pinscher (p<0.0001) and shih tzu (p<0.0001). Chihuahua had a significantly lower probability of calculus than Maltese (p<0.0001), Pomeranian (p<0.0001) and Yorkshire terriers (p<0.0001). The only other extra-small breed difference found was in the miniature poodle, which had increased risk of dental calculus when compared to the miniature pinscher (p<0.0001). The odds of a Yorkshire terrier having dental calculus was 1.49 times that of a Chihuahua (p<0.0001).

Figure 7B:
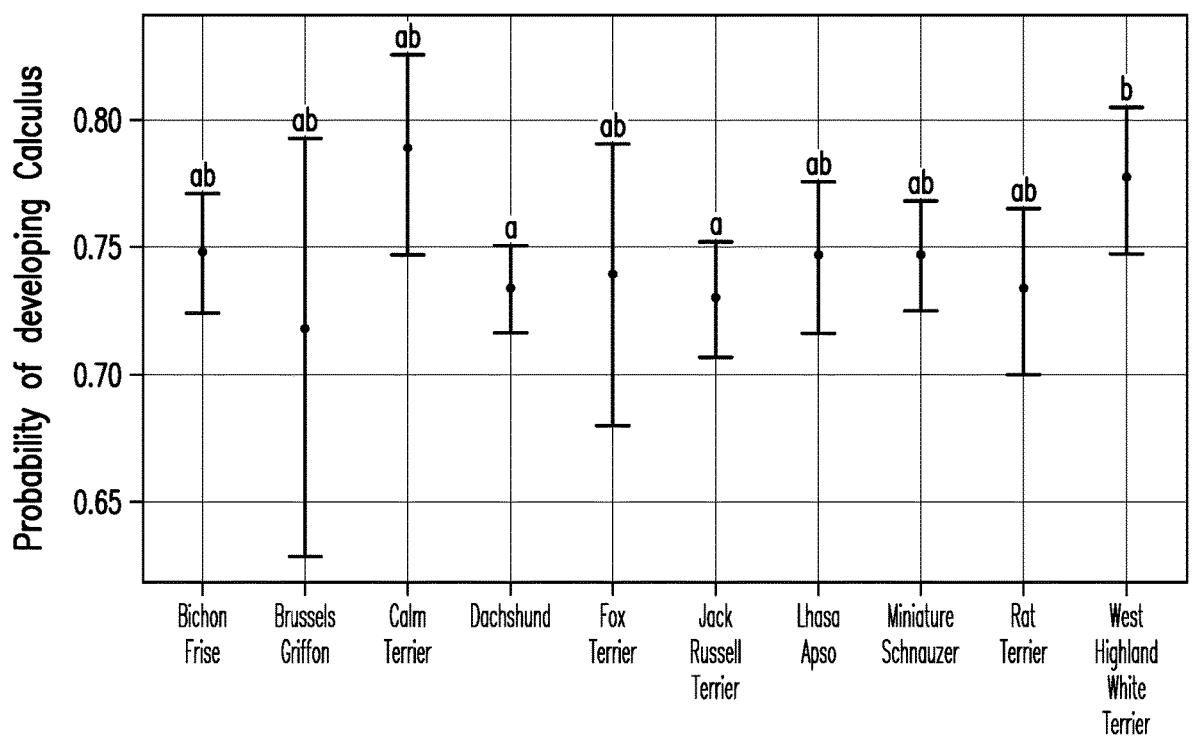

Investigation of inter-breed differences among the small breeds showed that almost all of the breeds were not significantly different in terms of risk for dental calculus (FIG. 7B). The exception was the West Highland white terrier which had a significantly increased probability of dental calculus compared to Jack Russell terriers (OR=0.69, p=0.0035) and dachshunds (OR=0.71, p=0.0027).

Figure 7C:
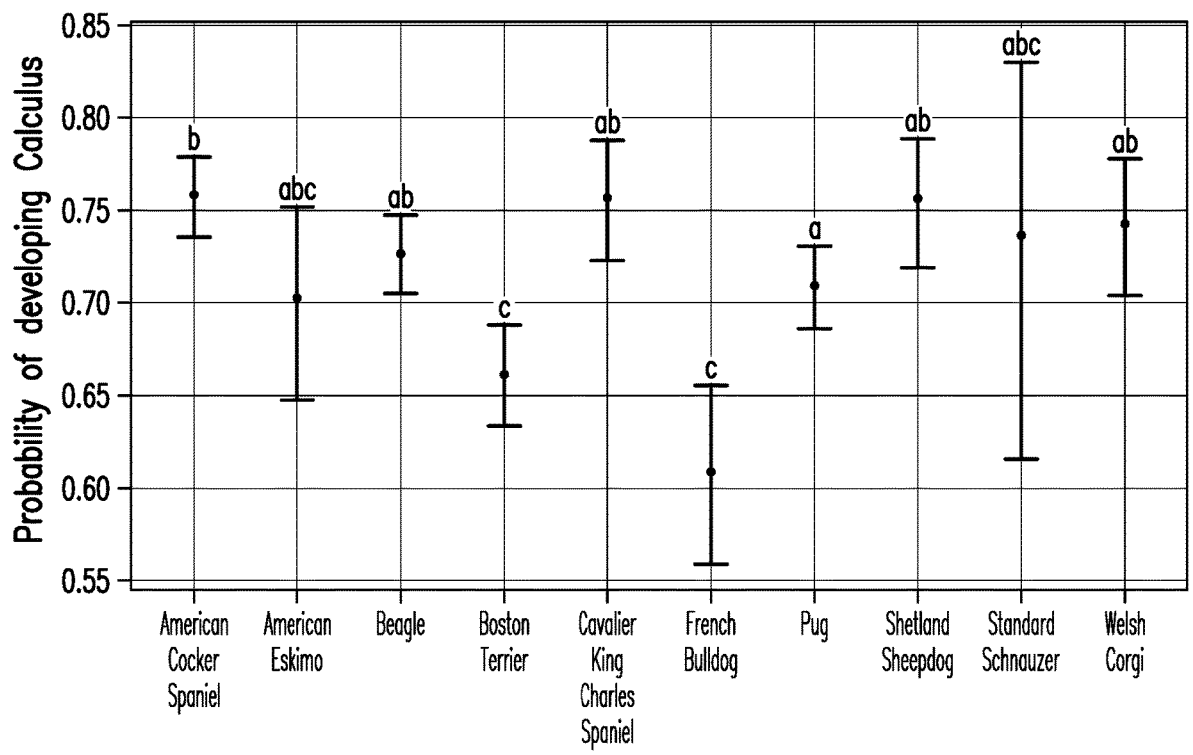

With respect to medium-small breeds the American cocker spaniel had a significantly higher probability of dental calculus than a Boston terrier (p<0.0001), French bulldog (p<0.0001) and pug (p<0.0001; FIG. 7C). The French bulldog and Boston terrier had a significantly lower probability of dental calculus than all other medium-small breeds except the American Eskimo (p=0.0039 and p=1.0, respectively) and standard schnauzer (p=0.15 and p=1.0, respectively). The odds of an American cocker spaniel having dental calculus was 3.05 times that of a French bulldog.

Figure 7D:
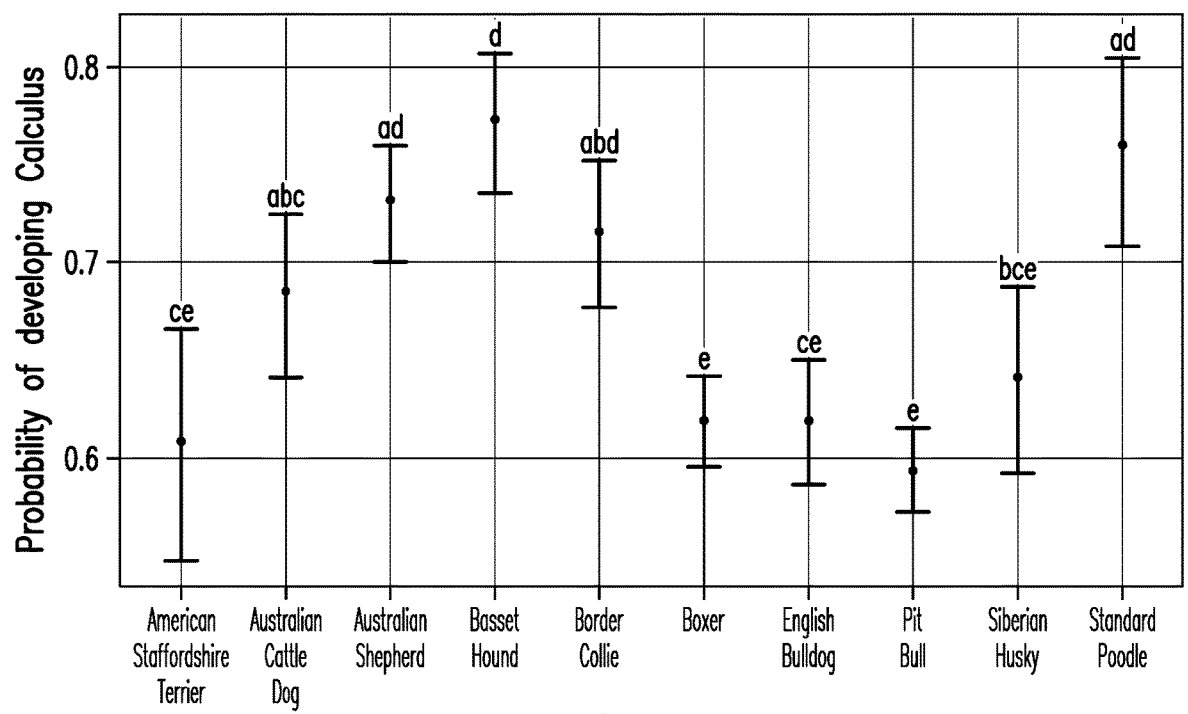

Inter-breed comparisons of the medium-large size category showed that basset hounds had a significantly higher probability of dental calculus than all other breeds (all p<0.0001; FIG. 7D) with the exception of Australian shepherd (p=0.26), border collie (p=0.033) and standard poodle (p=1.0). The boxer and pit bull had a significantly lower probability of dental calculus compared to all other breeds (p=0.001 to p<0.0001) with the exception of the American Staffordshire terrier, English bull dog and Siberian husky (p=0.06 to 1.0). The odds of a Basset hound having dental calculus was 4.57 times that of a pit bull.

Figure 7E:
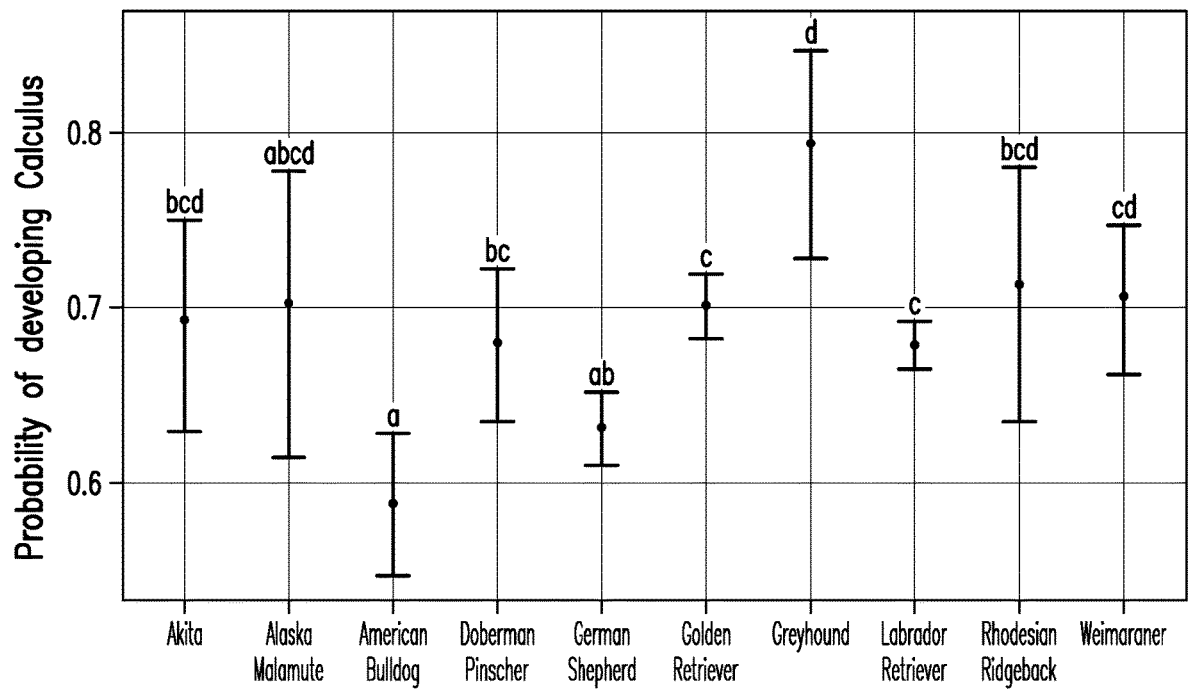

Pairwise comparison of the large breeds showed that greyhounds had the highest probability of dental calculus and this was significantly higher than the American bulldog (p<0.0001), Doberman pinscher (p=0.001), German shepherd (p<0.0001), Golden retriever (p=0.0035) and Labrador retriever (p<0.0001; FIG. 7E). American bulldog had a significantly lower probability of dental calculus than all other breeds (p=0.0022 to <0.0001) with the exception of the Alaskan malamute (p=0.03) and German shepherd (p=0.18). The odds of a greyhound having dental calculus was 5.46 times that of an American bulldog.

Figure 7F:
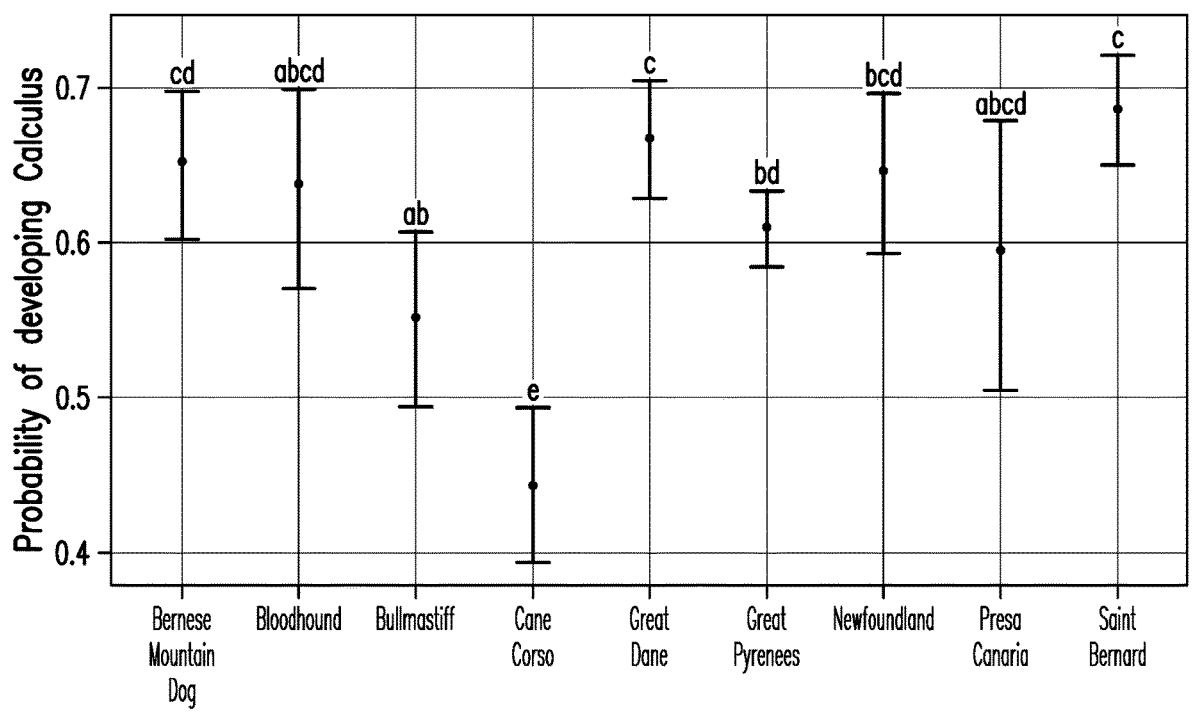

Pairwise comparison of the breeds within the giant breed size category showed that the cane corsa had a significantly lower probability of developing dental calculus than all other breeds (p=0.0009 to <0.0001; FIG. 7F). Great Dane and Saint Bernard had the highest probability of dental calculus but were not significantly different than Bernese mountain dog, bloodhound, Newfoundland and Presa Canaria (p=0.15 to 1.0). The odds of a Saint Bernard having dental calculus was 6.07 times that of a cane corsa (p<0.0001).

Example 2

Determination of Susceptibility Relying on Physical Features other Than Breed.

Further analysis of data for prevalence of PD across ca. 60 dog breeds, revealed that in addition to the effects of age and body weight, there was an effect from skull shape—

Figure 8:
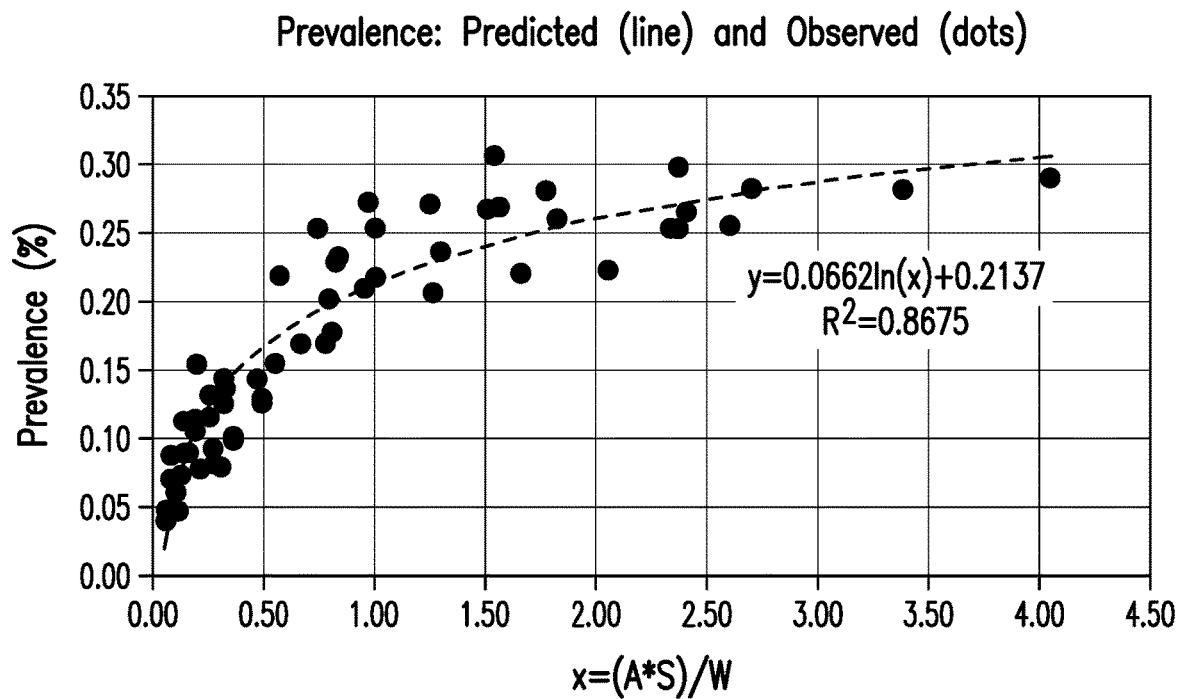
FIG. 8 is a graph showing the correlation between periodontal disease and a parameter determined using an algorithm in accordance with a method of the invention.
Figure 9:
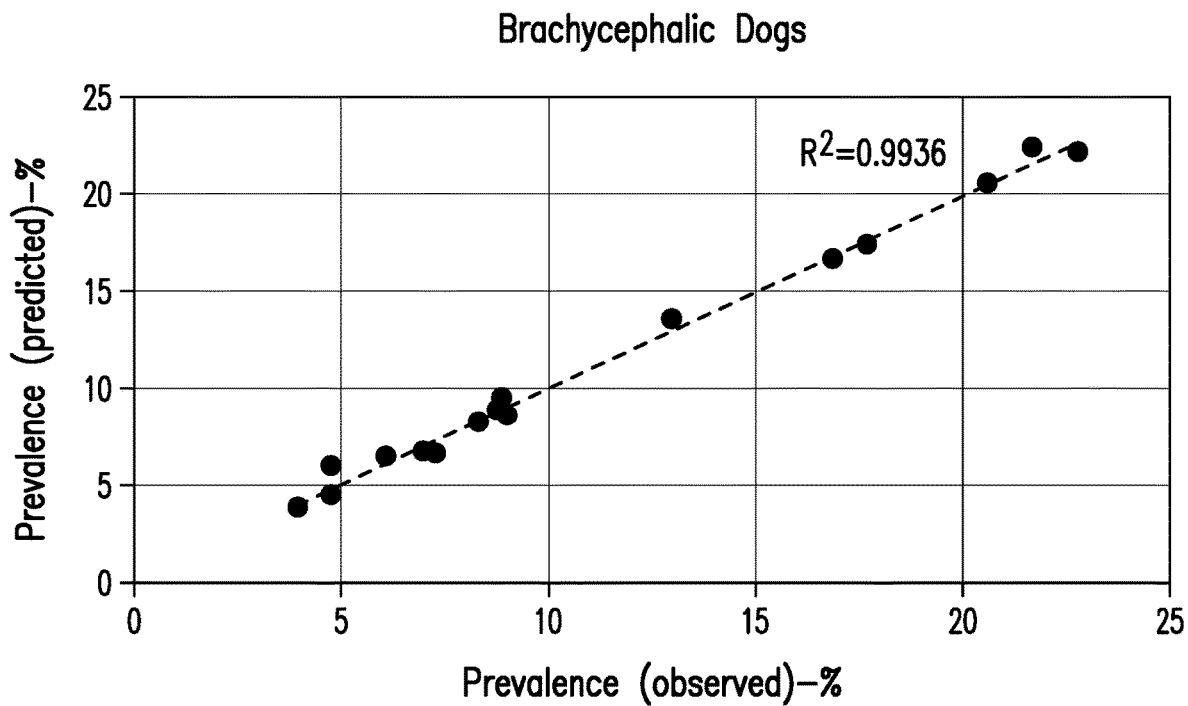
FIG. 9 is a graph showing the correlation between periodontal disease in brachyophilic dogs and a parameter determined using an alternative algorithm in accordance with a method of the invention.

In performing an analysis, the case of Greyhounds was omitted, since this breed seems to be truly exceptional. However, the relationship between prevalence of periodontal disease and an $R_p$ parameter as described in equation (1) above (i.e. (Age*Skull Type/Weight) was carried out. The correlation plot is shown in FIG. 8, with a respectable $R^2$ value of 0.87.

The close correlation indicates that this algorithm is particularly useful in the case of dogs for which breed information is unavailable. As a result, it is possible to provide a quantification of the risk value for dogs of various head sizes as follows:

Example 2a

Consider a large (30 kg), mesaticephalic dog, aged 2 years.

From Equation 1, $R_p=(2*2)/30=0.133$

From Equation 2, $L=0.0662*LN(0.133)+0.2137=0.080.$

From Table 3 above, this dog would be assessed as LOW risk for periodontal disease.

Example 2b

Consider a small (3 kg), mesaticephalic dog, aged 10 years.

From Equation 1, $R_p=(10*2)/3=6.67$

From Equation 2, $L=0.0662*LN(6.67)+0.2137=0.339.$

From Table 3 above, this dog would be assessed as HIGH risk for periodontal disease.

Example 2c

Consider a medium-sized (15 kg), dolichocephalic dog, aged 3 years.

From Equation 1, $R_p=(3*3)/15=0.60$

From Equation 2, $L=0.0662*LN(0.60)+0.2137=0.180.$

From Table 3 above, this dog would be assessed as MEDIUM risk for periodontal disease.

Example 2d

Consider again a medium-sized (15 kg), dolichocephalic dog, now aged 9 years.

From Equation 1, $R_p=(3*9)/15=1.80$

From Equation 2, $L=0.0662*LN(1.80)+0.2137=0.252.$

From Table 3 above, this dog would be assessed as MEDIUM-HIGH risk for periodontal disease.

Note that, comparing examples 2c and 2d confirms that, as expected, risk level increases with age.

TABLES

TABLE 8

Ten breeds of dog that most frequently visited a number of US vets over a five-year period, for each of the six breed size categories

| Extra-small (<6.5 kg) | Small (6.5 kg to <9 kg) | Medium-small (9 kg to <15 kg) | Medium-large (15 kg to <30 kg) | Large (30 kg to <40 kg) | Giant (>40 kg) |
|---|---|---|---|---|---|
| Chihuahua | Bichon Frise | American Cocker Spaniel | American Staffordshire Terrier | Akita | Bernese Mountain Dog |
| Maltese | Brussels Griffon | American Eskimo Dog | Australian Cattle Dog | Alaskan Malamute | Bloodhound |
| Miniature Pinscher | Cairn Terrier | Beagle | Australian Shepherd | American Bulldog | Bullmastiff |
| Miniature Poodle | Dachshund | Boston Terrier | Basset Hound | Doberman Pinscher | Cane Corso |
| Papillon | Fox Terrier | Cavalier King Charles Spaniel | Border Collie | German Shepherd | Great Dane |
| Pekingese | Jack Russell Terrier | French Bulldog | Boxer | Golden Retriever | Great Pyrenees |
| Pomeranian | Lhasa Apso | Pug | Pit Bull | Greyhound | Newfoundland |
| Shih Tzu | Miniature Schnauzer | Shetland Sheepdog | English Bulldog | Labrador Retriever | Presa Canaria |
| Toy Poodle | Rat Terrier | Standard Schnauzer | Siberian Husky | Rhodesian Ridgeback | Rottweiler |
| Yorkshire Terrier | West Highland White Terrier | Welsh Corgi | Standard Poodle | Weimeraner | Saint Bernard |

TABLE 9

Number and percentage of dogs and in-patient visits, for each of the six breed size categories

| Breed size category | Number of dogs | Percentage of dogs in study | Number of in-patient visits | Percentage of visits in study |
|---|---|---|---|---|
| Extra-small | 1,049,400 | 36.9% | 5,461,618 | 37.0% |
| Small | 379,413 | 13.4% | 2,175,047 | 14.7% |
| Medium-small | 331,010 | 11.7% | 1,939,830 | 13.2% |
| Medium-large | 469,655 | 16.5% | 2,115,592 | 14.3% |
| Large | 522,436 | 18.4% | 2,653,813 | 18.0% |
| Giant | 89,124 | 3.1% | 400,791 | 2.7% |
| Total | 2,841,038 | 100.0% | 14,746,691 | 100.0% |

TABLE 10

Summary of age, sex/neuter status, weight and body condition score at visit for each of the six breed size categories.

| Breed size category | Age (in months) | | Female | | Male | | Weight (kg) | | Body condition score | | |
|---|---|---|---|---|---|---|---|---|---|---|---|
| | Average (+/−stdev) | Range | Spayed | Intact | Neutered | Intact | Average (+/−stdev) | Range (10th percentile, 90th percentile) | Thin (1-3) | Normal (4-5) | Heavy (6-9) |
| Extra-small | 60.7 (+/−43.7) | 6.0-300.1 | 31.6% | 16.2% | 33.8% | 18.5% | 4.7 (+/−2.0) | 2.3-7.5 | 1.9% | 79.8% | 18.3% |
| Small | 74.7 (+/−46.4) | 6.0-296.7 | 37.8% | 8.9% | 41.3% | 12.0% | 7.6 (+/−2.3) | 4.7-10.7 | 1.2% | 71.0% | 27.9% |
| Medium-small | 69.3 (+/−44.3) | 6.0-298.5 | 38.7% | 8.1% | 41.4% | 11.8% | 12.1 (+/−3.8) | 7.7-17.2 | 1.1% | 64.1% | 34.8% |
| Medium-large | 48.6 (+/−39.5) | 6.0-300.1 | 32.9% | 14.7% | 30.7% | 21.8% | 25.9 (+/−6.5) | 17.9-34.4 | 2.3% | 77.7% | 20.0% |
| Large | 60.9 (+/−43.3) | 6.0-293.9 | 39.1% | 8.5% | 38.1% | 14.3% | 34.2 (+/−7.7) | 24.5-44.4 | 2.2% | 69.4% | 28.4% |
| Giant | 45.9 (+/−36.0) | 6.0-264.0 | 32.9% | 13.3% | 32.2% | 21.6% | 45.7 (+/−11.5) | 31.7-61.0 | 3.1% | 78.4% | 18.5% |

TABLE 11

Summary of age, sex/neuter status, weight and body condition score for the breeds of dog that most frequently visited a number of US vets (top 10 breeds in each breed size category).

| Breed | Age (months) | | Female | | Male | | Weight (kg) | | Body condition score | | |
|---|---|---|---|---|---|---|---|---|---|---|---|
| | Average (+/−stdev) | Range | Spayed | Intact | Neutered | Intact | Average (+/−stdev) | Range (10th percentile, 90th percentile) | Thin | Normal | Heavy |
| Chihuahua | 57.6 (+/−42.3) | 6.0-300.1 | 32.5% | 19.5% | 29.5% | 18.4% | 3.8 (+/−1.6) | 2.0-5.9 | 2.2% | 73.9% | 23.9% |
| Maltese | 61.3 (+/−43.1) | 6.0-276.1 | 31.2% | 14.4% | 36.7% | 17.7% | 4.3 (+/−1.6) | 2.5-6.4 | 2.0% | 85.2% | 12.8% |
| Miniature Pinscher | 71.4 (+/−45.5) | 6.0-294.3 | 35.6% | 13.0% | 37.0% | 14.5% | 5.8 (+/−2.1) | 3.3-8.7 | 1.8% | 63.6% | 34.6% |
| Miniature Poodle | 76.0 (+/−48.6) | 6.0-275.9 | 33.4% | 12.1% | 39.4% | 15.1% | 5.6 (+/−2.2) | 3.1-8.5 | 2.3% | 83.0% | 14.7% |
| Papillon | 68.4 (+/−42.0) | 6.0-253.0 | 37.1% | 10.2% | 41.7% | 11.0% | 4.8 (+/−2.0) | 2.6-7.4 | 2.2% | 81.7% | 16.1% |
| Pekingese | 78.9 (+/−47.8) | 6.0-281.8 | 31.9% | 13.8% | 36.3% | 18.0% | 6.5 (+/−1.7) | 4.4-8.8 | 2.1% | 83.1% | 14.9% |
| Pomeranian | 67.8 (+/−45.6) | 6.0-300.1 | 29.3% | 16.5% | 35.6% | 18.6% | 4.7 (+/−1.9) | 2.5-5.8 | 1.5% | 77.1% | 21.4% |
| Shih Tzu | 60.4 (+/−44.0) | 6.0-288.1 | 32.1% | 14.0% | 35.3% | 18.6% | 6.4 (+/−1.8) | 4.2-8.8 | 1.4% | 82.9% | 15.8% |
| Toy Poodle | 69.6 (+/−47.9) | 6.0-257.3 | 35.5% | 14.5% | 33.7% | 16.3% | 4.3 (+/−1.7) | 2.3-6.5 | 2.7% | 84.8% | 12.5% |
| Yorkshire Terrier | 54.6 (+/−40.5) | 6.0-288.1 | 28.9% | 16.2% | 34.3% | 20.7% | 3.9 (+/−1.7) | 2.0-6.1 | 1.9% | 84.1% | 14.0% |
| Bichon Frise | 76.8 (+/−46.4) | 6.0-278.1 | 34.4% | 8.2% | 46.0% | 11.5% | 7.2 (+/−2.2) | 4.6-10.2 | 0.8% | 74.9% | 24.2% |
| Brussels Griffon | 63.6 (+/−37.8) | 6.0-205.1 | 35.4% | 8.0% | 46.5% | 10.0% | 6.6 (+/−2.4) | 3.8-9.9 | 1.1% | 70.7% | 28.2% |
| Cairn Terrier | 78.7 (+/−45.3) | 6.0-264.1 | 39.4% | 5.8% | 48.1% | 6.7% | 8.4 (+/−2.2) | 5.8-11.3 | 0.5% | 59.7% | 39.8% |
| Dachshund | 72.4 (+/−46.2) | 6.0-286.3 | 38.1% | 9.5% | 39.4% | 13.1% | 6.7 (+/−2.0) | 4.3-9.4 | 1.3% | 65.2% | 33.5% |
| Fox Terrier | 81.4 (+/−46.6) | 6.0-252.1 | 40.9% | 8.1% | 41.2% | 9.9% | 7.8 (+/−3.2) | 3.6-12.0 | 1.7% | 75.1% | 23.2% |
| Jack Russell Terrier | 79.7 (+/−47.8) | 6.0-288.1 | 38.7% | 8.4% | 41.7% | 11.2% | 8.0 (+/−2.3) | 5.4-11.2 | 1.0% | 73.0% | 26.0% |
| Lhasa Apso | 82.4 (+/−48.2) | 6.0-296.7 | 35.5% | 9.4% | 43.5% | 11.6% | 8.3 (+/−2.3) | 5.5-11.3 | 1.6% | 75.0% | 23.4% |
| Miniature Schnauzer | 64.8 (+/−46.0) | 6.0-260.2 | 37.9% | 9.8% | 37.8% | 14.6% | 8.3 (+/−2.3) | 5.5-11.3 | 1.2% | 76.7% | 22.1% |
| Rat Terrier | 80.1 (+/−45.8) | 6.0-268.3 | 41.7% | 9.1% | 38.6% | 10.6% | 7.3 (+/−2.7) | 4.2-10.8 | 1.5% | 69.1% | 29.4% |
| West Highland White Terrier | 78.0 (+/−46.4) | 6.0-267.9 | 38.0% | 6.7% | 46.1% | 9.2% | 8.6 (+/−1.8) | 6.4-11.0 | 0.6% | 74.9% | 24.5% |
| American Cocker Spaniel | 79.1 (+/−46.0) | 6.0-298.5 | 38.3% | 9.3% | 39.6% | 12.8% | 13.1 (+/−3.3) | 9.1-17.6 | 1.3% | 66.2% | 32.4% |

TABLE 11-continued

Summary of age, sex/neuter status, weight and body condition score for the breeds of dog that most frequently visited a number of US vets (top 10 breeds in each breed size category).

| Breed | Age (months) Average (+/-stdev) | Range | Female Spayed | Female Intact | Male Neutered | Male Intact | Weight (kg) Average (+/-stdev) | Range (10th percentile, 90th percentile) | Body condition score Thin | Body condition score Normal | Body condition score Heavy |
|---|---|---|---|---|---|---|---|---|---|---|---|
| American Eskimo | 84.9 (+/−52.1) | 6.0-276.9 | 40.1% | 8.3% | 41.4% | 10.2% | 11.3 (+/−3.6) | 6.9-16.4 | 1.6% | 71.1% | 27.3% |
| Beagle | 72.8 (+/−44.3) | 6.0-280.8 | 42.0% | 6.9% | 41.0% | 10.1% | 14.4 (+/−4.1) | 9.5-20.0 | 1.1% | 56.9% | 42.0% |
| Boston Terrier | 57.9 (+/−40.5) | 6.0-240.6 | 38.4% | 7.3% | 41.7% | 12.6% | 9.9 (+/−2.6) | 6.8-13.5 | 1.2% | 82.8% | 16.1% |
| Cavalier King Charles Spaniel | 55.3 (+/−35.8) | 6.0-267.4 | 38.8% | 7.0% | 46.1% | 8.1% | 9.5 (+/−2.8) | 6.0-13.3 | 1.0% | 69.0% | 30.1% |
| French Bulldog | 37.2 (+/−28.8) | 6.0-262.1 | 33.3% | 9.5% | 40.3% | 17.0% | 11.4 (+/−2.4) | 8.4-14.5 | 0.9% | 84.7% | 14.5% |
| Pug | 68.4 (+/−41.8) | 6.0-274.8 | 36.5% | 9.0% | 41.5% | 13.0% | 10.0 (+/−2.4) | 7.1-13.2 | 0.7% | 52.4% | 47.0% |
| Shetland Sheepdog | 84.7 (+/−46.5) | 6.0-298.4 | 39.4% | 8.7% | 39.5% | 12.3% | 13.7 (+/−4.6) | 8.1-20.0 | 2.1% | 63.1% | 34.9% |
| Standard Schnauzer | 74.0 (+/−46.5) | 6.0-216.9 | 27.2% | 9.1% | 45.5% | 18.2% | 12.8 (+/−4.8) | 7.3-19.9 | 1.4% | 75.1% | 23.5% |
| Welsh Corgi | 65.6 (+/−42.9) | 6.0-264.1 | 39.2% | 6.4% | 44.8% | 9.6% | 13.8 (+/−3.5) | 9.5-18.5 | 0.7% | 62.3% | 37.0% |
| American Staffordshire Terrier | 52.9 (+/−40.5) | 6.0-287.1 | 35.4% | 13.2% | 30.1% | 21.2% | 27.4 (+/−6.1) | 19.8-35.5 | 1.5% | 77.3% | 21.3% |
| Australian Cattle Dog | 63.0 (+/−46.9) | 6.0-300.1 | 46.1% | 8.1% | 36.2% | 9.6% | 21.2 (+/−5.8) | 14.2-28.9 | 1.2% | 66.8% | 32.0% |
| Australian Shepherd | 58.3 (+/−45.2) | 6.0-241.8 | 41.4% | 7.3% | 41.6% | 9.7% | 20.7 (+/−7.6) | 10.3-30.4 | 1.2% | 70.0% | 28.8% |
| Basset Hound | 70.9 (+/−42.7) | 6.0-263.7 | 39.8% | 7.0% | 41.7% | 11.4% | 23.8 (+/−5.3) | 17.2-30.8 | 2.1% | 70.0% | 27.9% |
| Border Collie | 72.5 (+/−48.6) | 6.0-259.5 | 45.5% | 7.2% | 38.4% | 8.8% | 22.0 (+/−5.7) | 15.1-29.7 | 2.4% | 73.6% | 24.0% |
| Boxer | 49.7 (+/−36.1) | 6.0-253.1 | 37.3% | 9.6% | 36.3% | 16.8% | 28.1 (+/−6.1) | 20.6-36.3 | 3.4% | 81.0% | 15.6% |
| English Bulldog | 40.2 (+/−31.0) | 6.0-254.4 | 27.7% | 15.2% | 31.4% | 25.8% | 25.0 (+/−5.3) | 18.4-32.0 | 0.8% | 65.1% | 34.1% |
| Pit Bull | 37.6 (+/−34.0) | 6.0-253.9 | 25.9% | 21.5% | 22.0% | 30.6% | 27.2 (+/−6.0) | 19.7-35.2 | 2.1% | 82.8% | 15.1% |
| Siberian Husky | 53.6 (+/−44.0) | 6.0-235.4 | 36.3% | 12.6% | 35.7% | 15.4% | 24.6 (+/−5.9) | 17.7-32.9 | 4.7% | 83.4% | 11.9% |
| Standard Poodle | 65.0 (+/−44.1) | 6.0-254.6 | 37.1% | 8.0% | 43.9% | 11.1% | 24.4 (+/−5.4) | 18.0-31.8 | 3.9% | 89.2% | 7.0% |
| Akita | 59.0 (+/−44.0) | 6.0-213.2 | 33.4% | 14.3% | 31.4% | 20.9% | 37.9 (+/−8.6) | 27.0-49.3 | 2.8% | 80.6% | 16.6% |
| Alaskan Malamute | 58.5 (+/−43.5) | 6.0-229.1 | 36.4% | 9.3% | 41.4% | 12.9% | 39.6 (+/−10.4) | 26.8-54.0 | 1.5% | 71.0% | 27.4% |
| American Bulldog | 42.0 (+/−33.4) | 6.0-288.1 | 28.7% | 14.1% | 30.1% | 27.2% | 34.3 (+/−8.3) | 23.9-45.6 | 1.8% | 75.6% | 22.6% |
| Doberman Pinscher | 49.8 (+/−37.8) | 6.0-216.0 | 33.0% | 11.3% | 35.5% | 20.2% | 34.7 (+/−7.3) | 25.7-44.2 | 2.8% | 80.8% | 16.4% |
| German Shepherd | 49.2 (+/−40.4) | 6.0-279.7 | 35.2% | 12.5% | 31.3% | 21.1% | 34.2 (+/−7.9) | 24.4-44.7 | 4.7% | 82.9% | 12.4% |
| Golden Retriever | 67.3 (+/−43.7) | 6.0-275.9 | 41.9% | 6.6% | 41.9% | 11.4% | 34.3 (+/−7.1) | 25.4-43.7 | 1.5% | 62.8% | 35.7% |
| Greyhound | 88.5 (+/−36.6) | 6.0-225.4 | 50.6% | 1.7% | 46.0% | 1.7% | 30.8 (+/−4.7) | 25.1-36.9 | 5.5% | 92.5% | 2.0% |
| Labrador Retriever | 64.1 (+/−43.9) | 6.0-293.9 | 41.6% | 6.9% | 40.2% | 11.2% | 33.9 (+/−7.7) | 24.1-44.0 | 1.5% | 64.7% | 33.7% |
| Rhodesian Ridgeback | 58.1 (+/−41.1) | 6.0-224.3 | 39.9% | 7.3% | 41.1% | 11.7% | 38.1 (+/−8.8) | 26.8-49.8 | 2.1% | 75.8% | 22.1% |
| Weimaraner | 63.9 (+/−42.1) | 6.0-246.3 | 41.5% | 6.3% | 40.7% | 11.5% | 33.2 (+/−6.7) | 24.8-42.2 | 2.2% | 75.2% | 22.6% |
| Bernese Mountain Dog | 47.0 (+/−33.0) | 6.0-214.8 | 37.7% | 7.5% | 43.3% | 11.6% | 40.1 (+/−8.3) | 29.8-51.0 | 2.0% | 70.8% | 27.3% |
| Bloodhound | 45.1 (+/−33.7) | 6.0-180.1 | 34.8% | 11.4% | 35.5% | 18.4% | 40.9 (+/−9.7) | 29.0-54.0 | 3.0% | 74.2% | 22.8% |
| Bullmastiff | 44.5 (+/−32.4) | 6.0-204.8 | 31.3% | 12.5% | 30.5% | 25.8% | 47.3 (+/−10.9) | 33.1-61.7 | 1.2% | 72.1% | 26.6% |
| Cane Corso | 29.0 (+/−25.4) | 6.0-207.1 | 23.2% | 20.9% | 20.4% | 35.5% | 43.0 (+/−9.8) | 30.5-55.8 | 2.8% | 89.1% | 8.1% |
| Great Dane | 38.3 (+/−30.6) | 6.0-229.4 | 35.8% | 10.9% | 35.8% | 17.5% | 52.2 (+/−10.9) | 38.6-66.7 | 5.1% | 87.8% | 7.1% |
| Great Pyrenees | 48.5 (+/−36.8) | 6.0-263.5 | 37.5% | 8.9% | 40.7% | 12.9% | 42.7 (+/−10.3) | 29.8-56.6 | 4.4% | 79.1% | 16.5% |
| Newfoundland | 53.8 (+/−36.6) | 6.0-240.1 | 34.8% | 8.8% | 42.9% | 13.6% | 52.1 (+/−11.7) | 36.5-67.6 | 1.8% | 72.8% | 25.3% |
| Presa Canaria | 33.1 (+/−28.3) | 6.0-156.0 | 14.4% | 26.8% | 14.9% | 43.9% | 44.2 (+/−10.3) | 30.8-57.6 | 2.7% | 85.3% | 12.1% |
| Rottweiler | 51.9 (+/−39.6) | 6.0-264.0 | 31.3% | 15.4% | 28.0% | 25.4% | 41.4 (+/−9.5) | 29.5-54.1 | 2.1% | 72.7% | 25.2% |
| Saint Bernard | 46.6 (+/−34.0) | 6.0-218.7 | 34.9% | 12.3% | 36.3% | 16.6% | 53.5 (+/−11.8) | 38.7-68.9 | 4.2% | 83.3% | 12.5% |

TABLE 12

Percentage of pets and visits on wellness plan and average time on wellness plan

| Breed size category | Percentage pets on OWP | % Visits on OWP | Average time in months on OWP (+/-stdev) |
|---|---|---|---|
| Extra-small | 57.7% | 82.2% | 14.5 (+/−15.5) |
| Small | 55.0% | 81.1% | 15.5 (+/−16.2) |
| Medium-small | 56.1% | 81.6% | 15.2 (+/−15.9) |
| Medium-large | 57.6% | 80.3% | 12.7 (+/−14.5) |
| Large | 56.1% | 79.7% | 14.2 (+/−15.3) |
| Giant | 59.1% | 80.7% | 12.6 (+/−14.0) |

TABLE 13

Average number of dental cleanings during five-year study period, time since last dental cleaning and percentage of visits where a dental was performed.

| Breed size category | Average number of dental cleanings during five-year study period (+/−stdev) | At visit, time since last dental cleaning (% visits) | | | | Dental performed during visit |
|---|---|---|---|---|---|---|
| | | None known | In past 12 months | 12-24 months | >24 months | |
| Extra-small | 0.51 (+/−1.0) | 59.0% | 33.7% | 5.0% | 2.3% | 9.7% |
| Small | 0.62 (+/−1.1) | 52.3% | 39.0% | 6.0% | 2.8% | 10.7% |
| Medium-small | 0.53 (+/−1.2) | 57.5% | 34.5% | 5.5% | 2.5% | 9.0% |
| Medium-large | 0.26 (+/−0.8) | 74.6% | 20.8% | 3.1% | 1.5% | 5.8% |
| Large | 0.35 (+/−0.9) | 69.0% | 24.8% | 4.1% | 2.1% | 6.7% |
| Giant | 0.28 (+/−0.8) | 73.6% | 21.8% | 3.2% | 1.4% | 6.1% |

TABLE 14

Average number of dental cleanings, time since last dental cleaning and % of visits where a dental was performed for the 60 breeds of dog that most frequently visited a number of US vets (top 10 breeds in each breed size category).

| Breed size | Average number of dental cleanings (+/−stdev) | At visit, time since last dental cleaning (% visits) | | | | Dental performed during visit |
|---|---|---|---|---|---|---|
| | | None known | In past 12 mo. | 12-24 mo. ago | >24 mo. ago | |
| Chihuahua | 0.43 (+/−1.0) | 62.9% | 30.8% | 4.4% | 2.0% | 9.4% |
| Maltese | 0.58 (+/−1.1) | 55.4% | 36.4% | 5.7% | 2.5% | 10.3% |
| Miniature Pinscher | 0.54 (+/−1.1) | 55.0% | 36.8% | 5.7% | 2.5% | 10.2% |
| Miniature Poodle | 0.61 (+/−1.2) | 49.7% | 41.2% | 6.3% | 2.7% | 11.4% |
| Papillon | 0.67 (+/−1.2) | 49.9% | 41.9% | 5.8% | 2.5% | 12.3% |
| Pekingese | 0.46 (+/−1.0) | 57.9% | 33.3% | 5.7% | 3.2% | 8.8% |
| Pomeranian | 0.55 (+/−1.1) | 54.2% | 37.2% | 5.9% | 2.8% | 10.7% |
| Shih Tzu | 0.41 (+/−1.0) | 65.7% | 27.7% | 4.4% | 2.3% | 7.5% |
| Toy Poodle | 0.68 (+/−1.2) | 50.4% | 40.4% | 6.3% | 2.9% | 11.4% |
| Yorkshire Terrier | 0.61 (+/−1.1) | 55.3% | 37.5% | 5.3% | 203.0% | 10.8% |
| Bichon Frise | 0.67 (+/−1.2) | 49.9% | 40.5% | 6.7% | 3.0% | 10.5% |
| Brussels Griffon | 0.5 (+/−1.0) | 61.1% | 31.8% | 5.1% | 2.0% | 8.3% |
| Cairn Terrier | 0.64 (+/−1.2) | 51.6% | 39.2% | 6.4% | 2.9% | 10.8% |
| Dachshund | 0.66 (+/−1.2) | 50.3% | 41.5% | 5.7% | 2.5% | 11.7% |
| Fox Terrier | 0.6 (+/−1.2) | 50.4% | 39.5% | 6.7% | 3.4% | 10.5% |
| Jack Russell Terrier | 0.57 (+/−1.1) | 54.3% | 36.9% | 5.8% | 3.0% | 10.6% |
| Lhasa Apso | 0.53 (+/−1.1) | 54.1% | 36.2% | 6.4% | 3.3% | 9.3% |
| Miniature Schnauzer | 0.61 (+/−1.2) | 55.1% | 36.6% | 5.8% | 2.6% | 10.2% |
| Rat Terrier | 0.6 (+/−1.2) | 53.0% | 38.5% | 5.8% | 2.7% | 11.2% |
| West Highland White Terrier | 0.64 (+/−1.2) | 52.5% | 38.5% | 6.4% | 2.7% | 9.7% |
| American Cocker Spaniel | 0.57 (+/−1.1) | 51.3% | 39.0% | 6.5% | 3.2% | 9.4% |
| American Eskimo | 0.59 (+/−1.1) | 52.0% | 38.2% | 6.4% | 3.5% | 11.1% |
| Beagle | 0.57 (+/−1.1) | 54.6% | 36.8% | 5.9% | 2.7% | 9.6% |
| Boston Terrier | 0.35 (+/−0.9) | 70.9% | 23.4% | 3.7% | 201.0% | 6.4% |
| Cavalier King Charles Spaniel | 0.6 (+/−1.1) | 57.6% | 35.0% | 5.4% | 2.0% | 9.4% |
| French Bulldog | 0.26 (+/−0.7) | 79.2% | 17.3% | 2.5% | 0.9% | 4.2% |
| Pug | 0.53 (+/−1.1) | 57.6% | 34.9% | 5.4% | 2.2% | 8.9% |
| Shetland Sheepdog | 0.67 (+/−1.2) | 46.9% | 42.8% | 7.0% | 3.4% | 11.5% |
| Standard Schnauzer | 0.44 (+/−1.0) | 58.8% | 34.0% | 5.0% | 2.2% | 9.7% |
| Welsh Corgi | 0.56 (+/−1.1) | 57.4% | 35.7% | 4.8% | 2.0% | 1.1% |
| American Staffordshire Terrier | 0.31 (+/−0.8) | 71.3% | 23.5% | 3.5% | 1.7% | 6.4% |
| Australian Cattle Dog | 0.35 (+/−0.9) | 67.4% | 26.7% | 4.0% | 2.0% | 8.0% |
| Australian Shepherd | 0.39 (+/−0.9) | 67.2% | 26.8% | 3.9% | 2.1% | 8.0% |
| Basset Hound | 0.58 (+/−1.1) | 52.1% | 40.0% | 5.4% | 2.5% | 10.4% |
| Border Collie | 0.39 (+/−0.9) | 63.7% | 29.0% | 4.7% | 2.7% | 8.5% |
| Boxer | 0.31 (+/−0.8) | 73.2% | 21.9% | 3.4% | 1.5% | 5.8% |
| English Bulldog | 0.21 (+/−0.6) | 81.3% | 15.1% | 2.5% | 1.1% | 3.7% |
| Pit Bull | 0.16 (+/−0.6) | 83.0% | 14.3% | 1.9% | 0.9% | 4.2% |
| Siberian Husky | 0.32 (+/−0.8) | 71.7% | 22.4% | 3.7% | 2.2% | 6.5% |
| Standard Poodle | 0.52 (+/−1.1) | 56.7% | 35.1% | 5.4% | 2.7% | 9.2% |
| Akita | 0.34 (+/−0.9) | 68.3% | 24.6% | 4.4% | 2.6% | 7.3% |
| Alaskan Malamute | 0.33 (+/−0.8) | 69.3% | 24.5% | 4.3% | 1.9% | 6.9% |

TABLE 14-continued

Average number of dental cleanings, time since last dental cleaning and % of visits where a dental was performed for the 60 breeds of dog that most frequently visited a number of US vets (top 10 breeds in each breed size category).

| Breed size | Average number of dental cleanings (+/−stdev) | At visit, time since last dental cleaning (% visits) | | | | Dental performed during visit |
|---|---|---|---|---|---|---|
| | | None known | In past 12 mo. | 12-24 mo. ago | >24 mo. ago | |
| American Bulldog | 0.22 (+/−0.7) | 78.8% | 17.8% | 2.4% | 1.0% | 4.9% |
| Doberman Pinscher | 0.3 (+/−0.8) | 71.3% | 23.5% | 3.6% | 1.5% | 6.3% |
| German Shepherd | 0.25 (+/−0.7) | 75.8% | 19.8% | 3.0% | 1.4% | 5.7% |
| Golden Retriever | 0.38 (+/−0.9) | 66.3% | 26.7% | 4.6% | 2.5% | 7.0% |
| Greyhound | 0.76 (+/−1.2) | 37.8% | 53.3% | 6.7% | 2.2% | 14.3% |
| Labrador Retriever | 0.37 (+/−0.9) | 68.1% | 25.4% | 4.3% | 2.2% | 6.9% |
| Rhodesian Ridgeback | 0.43 (+/−1.0) | 62.6% | 30.8% | 4.9% | 1.8% | 8.2% |
| Weimaraner | 0.47 (+/−1.0) | 60.8% | 31.6% | 5.2% | 2.4% | 8.2% |
| Bernese Mountain Dog | 0.46 (+/−1.0) | 64.1% | 29.7% | 4.7% | 1.6% | 8.0% |
| Bloodhound | 0.26 (+/−0.7) | 73.3% | 22.5% | 3.1% | 1.2% | 5.9% |
| Bullmastiff | 0.25 (+/−0.7) | 76.4% | 18.6% | 3.0% | 2.0% | 4.9% |
| Cane Corso | 0.15 (+/−0.5) | 86.6% | 11.2% | 1.5% | 0.7% | 3.6% |
| Great Dane | 0.28 (+/−0.7) | 75.3% | 20.9% | 2.8% | 1.0% | 5.8% |
| Great Pyrenees | 0.29 (+/−0.8) | 71.1% | 24.5% | 3.1% | 1.3% | 6.8% |
| Newfoundland | 0.27 (+/−0.8) | 74.6% | 20.4% | 3.6% | 1.5% | 5.2% |
| Presa Canaria | 0.18 (+/−0.6) | 81.7% | 15.1% | 2.2% | 1.0% | 4.6% |
| Rottweiler | 0.27 (+/−0.8) | 72.3% | 22.6% | 3.4% | 1.7% | 6.3% |
| Saint Bernard | 0.29 (+/−0.8) | 73.0% | 22.2% | 3.4% | 1.3% | 6.4% |

TABLE 15

Percentage of dogs over five-year study period with periodontal disease and dental calculus, for each breed size category.

| Breed size category | Periodontal disease | | | | | Dental calculus (95% confidence interval) |
|---|---|---|---|---|---|---|
| | Total (95% Confidence interval) | Grade 1 | Grade 2 | Grade 3 | Grade 4 | |
| Extra-small | 22.4% (22.3, 22.5) | 11.5% | 7.3% | 5.1% | 3.0% | 78.3% (78.2, 78.3) |
| Small | 25.7% (25.6, 25.9) | 13.7% | 8.5% | 5.7% | 3.2% | 83.5% (83.4, 83.6) |
| Medium-small | 22.0% (21.9, 22.1) | 12.4% | 7.4% | 4.5% | 2.1% | 80.6% (80.5, 80.8) |
| Medium-large | 8.9% (8.8, 9.0) | 6.4% | 2.2% | 0.9% | 0.3% | 60.3% (60.1, 60.4) |
| Large | 11.9% (11.8, 12.0) | 8.5% | 3.3% | 1.1% | 0.3% | 71.0% (70.9, 71.1) |
| Giant | 9.1% (8.9, 9.3) | 6.6% | 2.5% | 0.7% | 0.2% | 63.7% (63.3, 64.0) |

TABLE 16

Percentage of dogs with periodontal disease and dental calculus for the 60 breeds of dog that most frequently visited a number of US vets (top 10 breeds in each breed size category).

| Breed size/Breed | Periodontal disease | | | | | Dental Calculus (95% confidence intervals) |
|---|---|---|---|---|---|---|
| | Total (95% confidence intervals) | Grade 1 | Grade 2 | Grade 3 | Grade 4 | |
| Chihuahua | 20.6% (20.5%-20.8%) | 10.2% | 6.4% | 4.8% | 3.0% | 74.5% (74.4%-74.7%) |
| Maltese | 25.4% (25.2%-25.7%) | 13.0% | 8.5% | 6.1% | 3.6% | 79.7% (79.4%-79.9%) |
| Miniature Pinscher | 22.2% (21.8%-22.6%) | 11.5% | 7.4% | 5.0% | 2.5% | 80.4% (80.0%-80.8%) |
| Miniature Poodle | 28.2% (28.0%-29.1%) | 13.3% | 10.2% | 7.1% | 4.6% | 83.1% (82.6%-83.6%) |
| Papillon | 29.7% (28.9%-30.4%) | 15.2% | 9.7% | 7.5% | 4.1% | 85.4% (84.8%-86.0%) |
| Pekingese | 21.7% (21.1%-22.2%) | 10.2% | 6.9% | 5.1% | 3.5% | 83.0% (82.5%-83.5%) |
| Pomeranian | 26.4% (26.1%-26.7%) | 12.4% | 8.7% | 6.8% | 4.2% | 81.6% (81.3%-81.9%) |
| Shih Tzu | 16.9% (16.7%-17.0%) | 10.2% | 5.1% | 2.8% | 1.5% | 77.0% (76.8%-77.2%) |
| Toy Poodle | 28.9% (28.5%-29.4%) | 13.5% | 10.1% | 7.7% | 4.7% | 82.5% (82.1%-82.9%) |
| Yorkshire Terrier | 25.4% (25.2%-25.6%) | 12.9% | 8.7% | 6.0% | 3.5% | 80.3% (80.1%-80.5%) |
| Bichon Frise | 27.9% (27.5%-28.3%) | 15.0% | 9.5% | 6.3% | 3.3% | 84.5% (84.2%-84.9%) |
| Brussels Griffon | 17.7% (16.4%-19.0%) | 10.9% | 5.2% | 3.2% | 1.3% | 80.2% (78.8%-81.5%) |
| Cairn Terrier | 26.8% (26.0%-27.6%) | 15.1% | 9.7% | 5.6% | 2.4% | 86.4% (85.8%-87.0%) |
| Dachshund | 28.1% (27.9%-28.4%) | 14.0% | 9.3% | 7.0% | 4.2% | 83.2% (83.0%-83.4%) |
| Fox Terrier | 25.6% (24.6%-26.7%) | 13.7% | 8.2% | 5.9% | 3.2% | 84.0% (83.1%-84.8%) |

TABLE 16-continued

Percentage of dogs with periodontal disease and dental calculus for the 60 breeds of dog that most frequently visited a number of US vets (top 10 breeds in each breed size category).

| Breed size/Breed | Total (95% confidence intervals) | Grade 1 | Grade 2 | Grade 3 | Grade 4 | Dental Calculus (95% confidence intervals) |
|---|---|---|---|---|---|---|
| Jack Russell Terrier | 22.0% (21.6%-22.3%) | 12.7% | 7.4% | 4.0% | 1.9% | 82.2% (81.9%-82.5%) |
| Lhasa Apso | 22.8% (22.4%-23.3%) | 12.0% | 7.5% | 5.1% | 2.7% | 85.0% (84.6%-85.4%) |
| Miniature Schnauzer | 23.7% (23.3%-24.1%) | 12.2% | 7.5% | 5.5% | 3.3% | 81.9% (81.6%-82.2%) |
| Rat Terrier | 26.0% (25.5%-26.6%) | 14.1% | 8.5% | 5.5% | 3.0% | 84.4% (83.9%-84.8%) |
| West Highland White Terrier | 26.6% (26.0%-27.2%) | 17.0% | 9.2% | 4.2% | 1.6% | 85.9% (85.5%-86.4%) |
| American Cocker Spaniel | 25.3% (24.9%-25.6%) | 13.6% | 9.1% | 5.4% | 2.6% | 84.7% (84.4%-85.0%) |
| American Eskimo | 27.0% (26.2%-27.9%) | 13.5% | 8.8% | 6.6% | 3.6% | 83.8% (83.1%-84.5%) |
| Beagle | 23.2% (22.9%-23.5%) | 13.8% | 7.9% | 4.2% | 1.8% | 82.7% (82.4%-82.9%) |
| Boston Terrier | 13.0% (12.7%-13.3%) | 8.5% | 3.4% | 1.8% | 0.7% | 72.8% (72.3%-73.2%) |
| Cavalier King Charles Spaniel | 27.3% (26.6%-27.9%) | 15.6% | 9.2% | 6.2% | 2.9% | 82.6% (82.1%-83.2%) |
| French Bulldog | 8.3% (7.8%-8.7%) | 6.2% | 1.8% | 0.6% | 0.2% | 61.9% (61.1%-62.7%) |
| Pug | 21.9% (21.6%-22.2%) | 10.9% | 7.4% | 5.3% | 2.8% | 80.4% (80.0%-80.7%) |
| Shetland Sheepdog | 30.6% (29.9%-31.2%) | 16.7% | 10.6% | 6.8% | 3.2% | 87.3% (86.8%-87.7%) |
| Standard Schnauzer | 21.0% (19.3%-22.7%) | 10.5% | 6.7% | 4.9% | 2.5% | 80.5% (78.8%-82.1%) |
| Welsh Corgi | 20.2% (19.6%-20.9%) | 13.1% | 6.2% | 3.2% | 1.0% | 80.7% (80.1%-81.3%) |
| American Staffordshire Terrier | 8.9% (8.4%-9.4%) | 6.9% | 1.9% | 0.6% | 0.2% | 62.9% (62.0%-63.8%) |
| Australian Cattle Dog | 12.6% (12.1%-13.0%) | 8.7% | 3.5% | 1.5% | 0.5% | 71.7% (71.0%-72.3%) |
| Australian Shepherd | 14.3% (14.0%-14.7%) | 10.3% | 4.1% | 1.5% | 0.4% | 73.9% (73.4%-74.3%) |
| Basset Hound | 25.3% (24.7%-26.0%) | 14.5% | 8.8% | 5.0% | 2.0% | 83.1% (82.6%-83.6%) |
| Border Collie | 15.4% (15.0%-15.9%) | 10.1% | 4.5% | 1.8% | 0.9% | 77.6% (77.0%-78.1%) |
| Boxer | 9.0% (8.8%-9.2%) | 6.6% | 2.1% | 0.8% | 0.2% | 63.9% (63.6%-64.2%) |
| English Bulldog | 7.3% (7.0%-7.5%) | 5.4% | 1.5% | 0.6% | 0.2% | 58.6% (58.2%-59.1%) |
| Pit Bull | 4.8% (4.7%-4.9%) | 3.9% | 1.0% | 0.2% | 0.1% | 49.3% (49.1%-49.5%) |
| Siberian Husky | 10.0% (9.5%-10.4%) | 7.5% | 2.4% | 0.8% | 0.3% | 65.4% (64.7%-66.1%) |
| Standard Poodle | 16.9% (16.1%-17.6%) | 11.1% | 5.3% | 2.1% | 0.8% | 79.0% (78.1%-79.8%) |
| Akita | 11.4% (10.7%-12.2%) | 7.9% | 3.5% | 1.3% | 0.2% | 71.0% (69.9%-72.0%) |
| Alaskan Malamute | 11.7% (10.7%-12.6%) | 8.3% | 3.3% | 1.1% | 0.3% | 72.3% (71.0%-73.6%) |
| American Bulldog | 6.1% (5.8%-6.4%) | 4.8% | 1.3% | 0.3% | 0.1% | 56.4% (55.8%-57.1%) |
| Doberman Pinscher | 10.1% (9.7%-10.6%) | 7.3% | 2.6% | 0.8% | 0.3% | 66.8% (66.0%-67.5%) |
| German Shepherd | 8.1% (8.0%-8.3%) | 5.9% | 2.1% | 0.6% | 0.2% | 61.0% (60.7%-61.3%) |
| Golden Retriever | 13.8% (13.6%-14.0%) | 10.0% | 3.9% | 1.2% | 0.3% | 77.7% (77.4%-78.0%) |
| Greyhound | 38.7% (37.4%-39.9%) | 17.1% | 12.3% | 11.9% | 6.4% | 89.2% (88.4%-90.0%) |
| Labrador Retriever | 12.6% (12.5%-12.8%) | 9.2% | 3.5% | 1.1% | 0.3% | 73.7% (73.5-73.8%) |
| Rhodesian Ridgeback | 13.1% (12.1%-14.0%) | 8.8% | 4.0% | 1.2% | 0.4% | 71.9% (70.6%-73.2%) |
| Weimaraner | 14.3% (13.7%-14.9%) | 10.4% | 4.2% | 1.3% | 0.3% | 75.7% (75.0%-76.4%) |
| Bernese Mountain Dog | 15.5% (14.3%-16.7%) | 11.2% | 5.5% | 1.3% | 0.2% | 73.9% (72.5%-75.3%) |
| Bloodhound | 9.3% (8.1%-10.6%) | 6.3% | 2.7% | 0.9% | 0.5% | 66.7% (64.6%-68.7%) |
| Bullmastiff | 7.0% (6.1%-7.9%) | 5.8% | 1.6% | 0.4% | 0.1% | 61.6% (59.8%-63.3%) |
| Cane Corso | 4.0% (3.4%-4.5%) | 3.4% | 0.6% | 0.2% | 0.0% | 42.9% (41.4%-44.4%) |
| Great Dane | 10.5% (10.1%-10.9%) | 7.7% | 2.8% | 0.8% | 0.2% | 63.0% (62.4%-63.7%) |
| Great Pyrenees | 11.4% (10.6%-12.2%) | 8.5% | 2.8% | 1.1% | 0.2% | 69.7% (68.6%-70.9%) |
| Newfoundland | 8.8% (7.8%-9.8%) | 6.8% | 2.4% | 0.5% | 0.1% | 71.2% (69.6%-72.8%) |
| Presa Canaria | 4.8% (3.6%-6.0%) | 3.9% | 0.8% | 0.2% | 0.2% | 49.6% (46.8%-52.4%) |
| Rottweiler | 7.8% (7.5%-8.0%) | 5.4% | 2.2% | 0.7% | 0.2% | 63.3% (62.8%-63.8%) |
| Saint Bernard | 11.2% (10.5%-12.0%) | 8.0% | 3.4% | 0.9% | 0.2% | 69.1% (68.0%-70.2%) |

The invention claimed is:

1. A method for treating periodontal diseases in a high-risk dog in need thereof, the method comprising:
determining an age of the dog in years, a skull shape categorization of the dog, and a weight of the dog in kilograms;
converting the skull shape categorization of the dog to a quantification of the skull shape, wherein the quantification of the skull shape is:
Brachycephalic skull: 1.0
Mesaticephalic skull: 2.0
Dolichocephalic skull: 3.0;
executing a first algorithm to calculate a risk parameter, wherein the first algorithm is based on a first equation represented by $Rp=(A*S)/W$, wherein A is the age of the dog in years, S is the quantification of the skull shape of the dog, W is the weight of the dog in kilograms, and Rp is the risk parameter;
executing a second algorithm to determine a risk level factor, wherein the second algorithm is based on a second equation represented by $L=0.0662*LN(Rp)+0.2137$, wherein LN is a natural logarithm with Rp as its input, and wherein L is the risk level factor;
determining a susceptibility level of the dog to periodontal diseases as follows:
Low risk when $L<0.10$
Low-Medium risk when $0.10<L<0.15$
Medium risk when $0.15<L<0.20$
Meidum-High risk when $0.20<L<0.30$
High risk when $L>0.30$; and administering an oral solution comprising at least chlorhexidine gluconate to the dog on a daily basis when the susceptibility level of the dog is high risk.

2. The method according to claim 1, further comprising:
determining a customized recommendation comprising recommendation for maintaining oral health of the dog; and
preparing the customized recommendation for the maintenance of oral health based on the susceptibility level.

3. The method according to claim 1, further comprising: determining the breed of the dog.

4. The method according to claim 2, wherein the customized recommendation further comprises at least one of the following:
a recommendation regarding nature and frequency of feeding of products which assist dental health or hygiene;
a recommendation regarding application or frequency of tooth brushing;
a recommendation regarding a size or nature of tooth cleaning products; and
a recommendation regarding an application or frequency of clinical
interventions such as deep cleaning procedures carried out by a veterinarian, wherein the cleaning procedures can be carried out by the veterinarian under anesthetic.

5. The method according to claim 4, wherein results of a subsequent review of periodontal health of the dog are used to modify the customized recommendation.

6. The method according to claim 5, wherein the subsequent review of the periodontal health comprises a test of swabs taken from a mouth of the dog.

7. The method of claim 1, further comprising a non-transitory computer-readable medium storing instructions that, when executed by a processor, cause a computer system to determine susceptibility level of a dog to periodontal diseases and determine or provide a customized recommendation for a treatment regimen for maintaining oral health of a dog, by performing the steps of the method.

8. A system for providing a treatment regimen for treating periodontal diseases in a high-risk dog in need thereof, the system comprising:
a processor; and
a memory that stores computer code that, when executed by the processor, causes the computer system to:
determine an age of the dog in years, a skull shape categorization of the dog, and a weight of the dog in kilograms;
convert the skull shape categorization of the dog to a quantification of the skull shape, wherein the quantification of the skull shape is:
Brachycephalic skull: 1.0
Mesaticephalic skull: 2.0
Dolichocephalic skull: 3.0;
execute a first algorithm to calculate a risk parameter, wherein the first algorithm is based on a first equation represented by Rp=(A*S)/W, wherein A is the age of the dog in years, S is the quantification of the skull shape of the dog, W is the weight of the dog in kilograms, and Rp is the risk parameter;
execute a second algorithm to determine a risk level factor, wherein the second algorithm is based on a second equation represented by L=0.0662*LN (Rp)+0.2137, wherein LN is a natural logarithm with Rp as its input, and wherein L is the risk level factor;
determine a susceptibility level of the dog to periodontal diseases as follows:
Low risk when L<0.10
Low-Medium risk when 0.10<L<0.15
Medium risk when 0.15<L<0.20
Meidum-High risk when 0.20<L<0.30
High risk when L>0.30; and
determine a treatment regimen comprising administrating an oral solution comprising at least chlorhexidine gluconate to the dog on a daily basis when the susceptibility level of the dog is high risk.

9. The system according to claim 8, wherein the computer system is caused to:
compare the weight or a body condition of the dog to an expected weight for a breed or an expected body condition of the dog;
generate a customized recommendation based on whether the dog is over or under weight or has a poor body condition.

10. The system according to claim 8, wherein the computer system is caused to:
receive an input comprising a dental review carried out on the dog, wherein determining the susceptibility level of the dog to periodontal diseases is further based on the input.

11. The system according to claim 10, wherein the dental review comprises an analysis of a mouth swab from the dog.

* * * * *